(12) United States Patent
Heibel et al.

(10) Patent No.: US 12,090,215 B2
(45) Date of Patent: Sep. 17, 2024

(54) METHOD AND DEVICE FOR DIRECT PRODUCTION OF RADIO-ISOTOPE BASED CANCER TREATMENT PHARMACEUTICALS

(71) Applicant: Westinghouse Electric Company LLC, Cranberry Township, PA (US)

(72) Inventors: Michael D. Heibel, Broomfield, CO (US); James Boyle, Aspinwall, PA (US); Kris Paserba, Butler, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 17 days.

(21) Appl. No.: 17/649,930

(22) Filed: Feb. 4, 2022

(65) Prior Publication Data
US 2023/0248853 A1  Aug. 10, 2023

(51) Int. Cl.
*A61K 51/04* (2006.01)
*A61K 51/08* (2006.01)
*A61K 51/12* (2006.01)

(52) U.S. Cl.
CPC ........ *A61K 51/0482* (2013.01); *A61K 51/088* (2013.01); *A61K 51/121* (2013.01); *A61K 2123/00* (2013.01); *C07B 2200/05* (2013.01)

(58) Field of Classification Search
CPC .............. A61K 51/0482; A61K 51/088; A61K 51/121; C07B 2200/05
USPC ....................................................... 424/1.69
See application file for complete search history.

(56) References Cited

U.S. PATENT DOCUMENTS

| 10,596,276 B2 | 3/2020 | de Palo et al. |
| 10,706,982 B2 | 7/2020 | Teleki |
| 2007/0160176 A1 * | 7/2007 | Wada ........................ G21G 1/06 376/158 |
| 2013/0129027 A1 * | 5/2013 | Pantell ..................... H05H 3/06 376/190 |
| 2013/0142296 A1 | 6/2013 | Piefer et al. |
| 2014/0294700 A1 | 10/2014 | Marx et al. |
| 2020/0131224 A1 * | 4/2020 | Fugazza ............... A61K 51/121 |

FOREIGN PATENT DOCUMENTS

| BR | 102013033622 A2 * | 7/2017 | ............... G02F 1/00 |
| CA | 2823960 C * | 8/2014 | ............... G21C 5/02 |
| JP | 2020038780 A | 3/2020 | |

OTHER PUBLICATIONS

Di Pasqua et al. J Nucl. Med. 2013, 54, 111-116. (Year: 2013).*
Chakravarty et al. Mol. Pharmaceutics 2014, 11, 3777-3797. (Year: 2014).*
Burgio et al. (IEEE Trans. Nucl. Sci. 2011, 58, 445-450.*
Di Pasqua et al. Small 2012, 8, 997-1000. (Year: 2012).*
Chakraborty et al., On the practical aspects of large-scale production of 177Lu for peptide receptor radionuclide therapy using direct neutron activation of 176Lu in a medium flux research reactor: the Indian experience, J Radioanal Nucl Chem (Apr. 29, 2014), 301(1):233-243.
International Search Report and Written Opinion for International PCT Application No. PCT/US2023/062015, dated Aug. 1, 2023.

* cited by examiner

*Primary Examiner* — Michael G. Hartley
*Assistant Examiner* — Sean R Donohue
(74) *Attorney, Agent, or Firm* — K&L Gates LLP

(57) ABSTRACT

The present disclosure is generally related to methods, systems and devices for direct production of a radioisotope-based cancer treatment pharmaceutical directly from a corresponding non-radioactive drug molecule precursor by irradiating the non-radioactive drug molecule precursor using neutrons produced by an electronic neutron generator array or other neutron generator sources.

20 Claims, 10 Drawing Sheets

METHOD AND DEVICE FOR DIRECT PRODUCTION OF RADIO-ISOTOPE BASED CANCER TREATMENT PHARMACEUTICALS

FIELD

The present disclosure is generally related to methods, systems and devices for production of radioisotope pharmaceuticals, more particularly, is directed to improved methods, systems and devices for direct production of radioisotope based cancer treatment pharmaceuticals by irradiating corresponding non-radioactive drug molecule precursors using neutrons generated by an electronic neutron generator array to convert at least part of the non-radioactive drug molecule precursors to the radioisotope pharmaceuticals.

SUMMARY

The following summary is provided to facilitate an understanding of some of the innovative features unique to the aspects disclosed herein, and is not intended to be a full description. A full appreciation of the various aspects can be gained by taking the entire specification, claims, and abstract as a whole.

In various aspects, the present disclosure provides devices, systems and methods for direct production of a radioisotope pharmaceutical directly from a corresponding non-radioactive drug molecule precursor by irradiating the non-radioactive drug molecule precursor using neutrons generated by an electronic neutron generator array or other neutron emitting material such as Californium-252 (Cf-252) sources.

In various aspects, the present disclosure provides a method for producing a radioisotope pharmaceutical directly from a corresponding non-radioactive drug molecule precursor. The method comprises irradiating the non-radioactive drug molecule precursor using neutrons generated by an electronic neutron generator array or other neutron emitting material; and converting at least part of the non-radioactive drug molecule precursor to the radioisotope pharmaceutical.

In various aspects, the method comprises preparing the non-radioactive drug molecule precursor.

In various aspects, the radioisotope pharmaceutical comprises a radionuclide or a radioactive isotope of a metal or metal ion.

In various aspects, the non-radioactive drug molecule precursor comprises a non-radioactive isotope of the same metal or metal ion as the metal or metal ion in the radioisotope pharmaceutical. In embodiments, the non-radioactive drug molecule precursor has the same chemical structure as that of the radioisotope pharmaceutical except that the radioactive isotope of the metal or metal ion in the radioisotope pharmaceutical is replaced by its corresponding non-radioactive isotope of the metal or metal ion.

In various aspects, the non-radioactive drug molecule precursor comprises a non-radioactive isotope of a second metal or metal ion different from the metal or metal ion in the radioisotope pharmaceutical.

In various aspects, the radioisotope pharmaceutical is for treatment of a cancer or tumor including neuroendocrine tumor (NET), gastroenteropancreatic neuroendocrine tumor (GEP-NET), prostate cancer, lung cancer, non-Hodgkin lymphoma, bone pain palliation and others.

Non-limiting examples of the radioisotope pharmaceutical include a Lu-177 based radioisotope pharmaceutical such as Lu-177 dotatate, an iodine-131 (I-131) based radioisotope pharmaceutical such as I-131 tositumomab, and a yttrium-90 (Y-90) based radioisotope pharmaceutical such as Y-90 ibritumomab-tiuxetan.

In various aspects, the method of the present disclosure can be applied to produce any other radioisotope-based cancer treatment pharmaceuticals which can be prepared by irradiating a non-radioactive isotope drug molecule precursor through short-term neutron exposure.

In various aspects, the radioisotope pharmaceutical is a Lu-177 based radioisotope pharmaceutical, and the non-radioactive drug molecule precursor is a Lu-176 drug molecule precursor. In embodiments, the Lu-176 drug molecule precursor has the same chemical structure as that of the Lu-177 based radioisotope pharmaceutical except that the Lu-177 in the Lu-177 based radioisotope pharmaceutical is replaced by Lu-176. In embodiments, the Lu-177 based radioisotope pharmaceutical is produced by irradiating the Lu-176 drug molecule precursor using neutrons generated by the electronic neutron generator array to convert at least part of the Lu-176 to Lu-177.

In various aspects, the radioisotope pharmaceutical is Lu-177 dotatate, and the non-radioactive drug molecule precursor is Lu-176 dotatate. In embodiments, the Lu-177 dotatate is directly produced by irradiating the Lu-176 dotatate using neutrons to convert at least part of the Lu-176 in the Lu-176 dotatate to Lu-177.

In various aspects, the radioisotope pharmaceutical is a I-131 based radioisotope pharmaceutical, and the non-radioactive drug molecule precursor is a tellurium (Te) drug molecule precursor. In embodiments, the I-131 based radioisotope pharmaceutical is produced by irradiating the Te drug molecule precursor using neutrons generated by the electronic neutron generator array to convert at least part of the Te in the Te drug molecule precursor to I-131.

In various aspects, the radioisotope pharmaceutical is I-131 tositumomab, and the non-radioactive drug molecule precursor is tellurium tositumomab. In embodiments, the I-131 tositumomab is produced by irradiating the tellurium tositumomab using neutrons.

In various aspects, the radioisotope pharmaceutical is the yttrium-90 (Y-90) based radioisotope pharmaceutical, and the non-radioactive drug molecule precursor is a yttrium-89 (Y-89) drug molecule precursor. In embodiments, the Y-90 based radioisotope pharmaceutical is produced by directly irradiating the Y-89 drug molecule precursor using neutrons generated by the electronic neutron generator array.

In various aspects, the radioisotope pharmaceutical is Y-90 ibritumomab-tiuxetan, and the non-radioactive drug molecule precursor is Y-89 ibritumomab-tiuxetan. In embodiments, the Y-90 ibritumomab-tiuxetan is produced by directly irradiating the Y-89 ibritumomab-tiuxetan using neutrons generated by the electronic neutron generator array.

In embodiments, the method may not need or exclude any further chemical reactions after the conversion.

In various aspects, the method further comprises a process for preparing the non-radioactive drug molecule precursor.

In various aspects, the radioisotope pharmaceutical comprises or is a first complex of a radionuclide and a target cell binding moiety linked to a chelating agent.

In various aspects, the non-radioactive drug molecule precursor comprises or is a second complex of a corresponding non-radioactive isotope of the radionuclide and the target cell binding moiety linked to the chelating agent. In various aspects, the process for preparing the non-radioactive drug molecule precursor comprises: 1) providing a first aqueous solution comprising the corresponding non-radioactive isotope of the radionuclide; 2) providing a second aqueous solution comprising the target cell receptor binding peptide linked to the chelating agent; 3) mixing the first and second solutions provided in steps 1) and 2) to form a mixture; and 4) heating the mixture to form a reacted solution comprising the second complex of the corresponding non-radioactive isotope of the radionuclide and the target cell receptor binding peptide linked to the chelating agent to form the non-radioactive drug molecule precursor.

In various aspects, the process further comprises drying the reacted solution to form a solid or a concentrate comprising the second complex of the non-radioactive isotope and the target cell receptor binding moiety linked to the chelating agent to form the non-radioactive drug molecule precursor, preferably to form a solid.

In various aspects, the process comprises treating the reacted solution comprising the second complex to obtain the second complex in solid form.

In various aspects, the target cell receptor binding moiety is a target cell receptor binding peptide.

In various aspects, the method for producing the radioisotope pharmaceutical comprises irradiating the non-radioactive drug molecule precursor (comprising or being the second complex) to convert at least part of the non-radioactive isotope in the second complex to the radionuclide to thus form the radioisotope pharmaceutical (comprising or being the first complex).

In various aspect, the radioisotope pharmaceutical is Lu-177 based radioisotope pharmaceutical, and the non-radioactive drug molecule precursor is Lu-176 drug molecule precursor. The process for preparing the Lu-176 drug molecule precursor comprise: 1) providing a first aqueous solution comprising the non-radioactive Lu-176 isotope; 2) providing a second aqueous solution comprising a target cell receptor binding moiety (such as peptide) linked to a chelating agent; 3) mixing the first and second solutions provided in steps 1) and 2) to form a mixture; and 4) heating the mixture to form a reacted solution comprising a complex of Lu-176 and the target cell receptor binding moiety linked to the chelating agent to form the Lu-176 drug molecule precursor.

In various aspect, the radioisotope pharmaceutical is Lu-177 dotatate which is a complex, and the non-radioactive drug molecule precursor is Lu-176 dotatate. The process for preparing the Lu-176 dotatate comprise: 1) providing a first aqueous solution comprising the non-radioactive Lu-176 isotope; 2) providing a second aqueous solution comprising dotatate; 3) mixing the first and second solutions provided in steps 1) and 2) to form a mixture; and 4) heating the mixture to form a reacted solution comprising Lu-176 dotatate which is a complex.

In various aspect, the first aqueous solution comprises $LuCl_3$ (Lu-176) and HCl.

In various aspect, the process comprises treating the reacted solution comprising the Lu-176 dotatate to form Lu-176 dotatate in a solid or concentrate form, preferably in the solid form.

In various aspects, the method for producing Lu-177 dotatate comprises irradiating Lu-176 dotatate using neutrons generated by neutron generators to convert at least part of the Lu-176 in Lu-176 dotatate to Lu-177 to form Lu-177 dotatate.

In various aspects, the present disclosure provides devices, systems and methods for direct production of Lu-177 based radioisotope pharmaceuticals from non-radioactive Lu-176 precursor compounds or complexes using neutrons produced by an electronic neutron generator array or other neutron emitting material such as Californium-252 (Cf-252) sources. The Lu-177 based radioisotope pharmaceuticals are used for localized treatments of target cells (such as tumor or cancer cells) having overexpression of cell receptors compared to normal tissues. The Lu-177 based radioisotope pharmaceuticals include a target cell receptor binding moiety that has at least one binding site that binds to the target cell receptors. Therefore, the Lu-177 based radioisotope pharmaceutical, after administration to a patient in need thereof, is specifically delivered to and binds to the target cells (such as tumor or tumor-associated cells) of the patient for tumor therapeutic targeting or imaging and substantially leaves the normal cells unaffected.

In various aspects, a method for producing a Lu-177 based radioisotope pharmaceutical directly from a Lu-176 complex or compound using neutrons generated by an electronic neutron generator array or other neutron emitting material sources is disclosed herein. The method comprises: 1) providing a first aqueous solution comprising the non-radioactive Lu-176 isotope; 2) providing a second aqueous solution comprising a target cell receptor binding peptide linked to a chelating agent; 3) mixing the first and second solutions provided in steps 1) and 2) to form a mixture; 4) heating the mixture to form a reacted solution comprising a complex of Lu-176 and the target cell receptor binding peptide linked to the chelating agent; and 5) irradiating the complex to convert at least part of Lu-176 isotope to Lu-177 radioisotope in the complex to form the Lu-177 based radioisotope pharmaceutical.

In various aspects, the method further comprises drying the reacted solution to form a solid or a concentrate comprising the complex of Lu-176 and the target cell receptor binding peptide linked to the chelating agent before irradiating the complex in step 5), preferably to form a solid.

In various aspects, the target cell receptor binding peptide comprises or is a somatostatin receptor binding peptide. In embodiments, the somatostatin receptor binding peptide is selected from octreotide, octreotate, lanreotide, vapreotide and pasireotide, preferably selected from octreotide and octreotate. In embodiments, the somatostatin receptor binding peptide is octreotate. Other target cell receptor binding peptides are contemplated by the present disclosure.

In various aspects, the chelating agent is selected from the group consisting of DOTA, DTPA, NT, EDTA, DO3A, NOC and NOTA. In embodiments, the chelating agent comprises or is DOTA. Other chelating agents are completed by the present disclosure.

In various aspects, the target cell receptor binding peptide linked to the chelating agent comprises or is selected from the group consisting of DOTA-OC, DOTA-TOC (edotreotide), DOTA-NOC, DOTA-TATE (oxodotreotide), DOTA-LAN, and DOTA-VAP.

In various aspects, the target cell receptor binding peptide linked to the chelating agent comprises or is DOTA-TATE (dotatate or oxodotreotide) or DOTA-TOC (dotatoc or edotreotide). In embodiments, the target cell receptor binding peptide linked to the chelating agent comprises or is DOTA-TATE (dotatate or oxodotreotide).

In various aspects, the complex comprises or is Lu-176 dotatoc or Lu-176 dotatate (the drug molecule precursor). In embodiments, the complex comprises or is Lu-176 dotatate.

In various aspects, the Lu-177 based radioisotope pharmaceutical comprises or is Lu-177 dotatoc or Lu-177 dotatate (the final drug). In embodiments, the Lu-177 based radioisotope pharmaceutical comprises or is Lu-177 dotatate.

In various aspects, the method may exclude using any radioisotope intermediate compounds. In various aspects, the method may exclude using any Lu-177 intermediate compounds.

In various aspects, the method may further comprise adding one or more stabilizers selected from gentisic acid, ascorbic acid, and a salt thereof to the reacted solution in step 4) discussed above to improve the stability of the Lu-177 based radioisotope pharmaceutical, such as Lu-177 dotatate.

In various aspects, the method may exclude using any stabilizer (such as gentisic and ascorbic acids and their salts and ethanol) in the production of the Lu-177 radioisotope pharmaceuticals.

In various aspects, the present disclosure provides a device for producing a radioisotope pharmaceutical directly from a non-radioactive drug molecule precursor by irradiating the non-radioactive drug molecule precursor using neutrons or a thermal neutron flux generated by an electronic neutron generator array or other neutron emitting material such as Californium-252 (Cf-252) sources. The device comprises: 1) an electronic neutron generator array or at least one neutron emitting material source configured to generate neutrons or a thermal neutron flux; 2) an irradiation module; and 3) an irradiation module insert. In embodiments, the device comprises the electronic neutron generator array including at least one electronic neutron generator.

In various aspects, the irradiation module comprises an irradiation module insertion tube; a Deuterium Oxide "$D_2O$" moderator module housing $D_2O$ with adjustable thickness surrounding and attached to the outer side surface of the Irradiation module insertion tube; a borated water module surrounding and attached to the outer side surface of the $D_2O$ moderator module; and a metallic shielding module surrounding and attached to the outer surface of the borated water module. In embodiments, the irradiation module insertion tube has an insertion port for placing the irradiation module insert into the irradiation module insertion tube.

In various aspects, the borated water module is configured to house a borated water composition comprising 8-12 wt. % of sodium borate, 8-40 wt. % or preferably 8-20 wt. % of boric acid, and balance water. One of the advantages of using the borated water composition is that the water enriched with borate can achieve the same shielding effects at reduced water volume as compared to normal water.

In various aspects, the at least one electronic neutron generator are configured to be placed in a same plane and direct their neutrons or neutron flux to the center (middle section) of the Irradiation module insertion tube of the irradiation module. In embodiments, the at least one electronic neutron generator are configured to be placed in various planes and to direct their neutrons or neutron flux to the center of the Irradiation module insertion tube of the irradiation module from different angles.

In various aspects, the irradiation module insert comprises an insertion rode; a removable nose configured to detachably connect to the insertion rod; an irradiation chamber housed in the removable nose; an insertion position lock ring configured to be placed on the insertion rod for locking irradiation module insert with the insertion port to adjust the position of the irradiation chamber in the Irradiation module insertion tube when the irradiation module insert is inserted into the Irradiation module insertion tube; a radiation detector surrounding and/or attached to the irradiation chamber for detecting the irradiation level from the irradiation chamber; and a temperature sensor coupled to the irradiation chamber for sensing the temperature of the irradiation chamber.

In various aspects, the device may further comprise a target cooling unit including a liquid coolant. In embodiments, the target cooling unit is configured to attach to the irradiation module to circulate the coolant through the Irradiation module insertion tube for cooling the Irradiation module insertion tube and thus the irradiation chamber of the irradiation module insert when inserted into the Irradiation module insertion tube.

In various aspects, the device may further comprise a control unit configured to attach to the irradiation module and the irradiation module insert.

In various aspects, the irradiation module insert further comprises an irradiation detector signal output configured to deliver a first signal of the detected irradiation level from the radiation detector to the control unit; and a temperature sensor signal output configured to deliver a second signal of the sensed temperature from the temperature sensor to the control unit.

In various aspects, the irradiation module insert is configured to be placed into the Irradiation module insertion tube and keep the irradiation chamber at the center (middle section) of the Irradiation module insertion tube and also at the center of the at least one electronic neutron generator so that the neutron flux from the at least one electronic neutron generators are all directed to the irradiation chamber.

In various aspects, the irradiation module insert is configured to allow an irradiation source (or target) material to be placed into the irradiation chamber housed inside the removable nose.

In various aspects, the irradiation chamber is a hollow cylinder for housing an irradiation source (or target) material, and the irradiation detector is a hollow cylinder concentric with the irradiation chamber and configured to surround at least a portion or the entire outer side (curved) surface of the irradiation chamber, preferably the entire outer side surface of the irradiation chamber. In embodiments, the irradiation detector may or may not cover the top and bottom round surfaces of the irradiation chamber.

In various aspects, the Irradiation module insertion tube is configured to be in a cylinder shape so that the irradiation module insert can be freely inserted into and removed from the Irradiation module insertion tube.

In various aspects, the target cooling unit is configured to circulate the coolant through the Irradiation module insertion tube so to control the temperatures inside the Irradiation module insertion tube and thus the irradiation chamber of the irradiation module insert when inserted into the Irradiation module insertion tube.

In various aspects, the control unit is configured to: 1) receive the first and second signals from the radiation detector and the temperature sensor; 2) adjust parameters of the target cooling unit to control the temperature inside the Irradiation module insertion tube and the irradiation chamber to be maintained within a predetermined temperature range; 3) determine whether the detected irradiation level reaches a predetermined level; and 4) turn off the at least one electronic neutron generator when the detected irradiation level reaches the predetermined level.

In various aspects, the device does not include the target cooling unit. In various aspects, the device does not include the control unit. In various aspects, the device is configured to connect to an external target cooling unit and/or an external control unit.

In various aspects, the radioisotope pharmaceutical is a radioisotope-based cancer treatment pharmaceuticals. Non-limiting examples of the radioisotope pharmaceutical include a Lu-177 based radioisotope pharmaceutical such as Lu-177 dotatate, an iodine-131 (I-131) based radioisotope pharmaceutical such as I-131 tositumomab, and a yttrium-90 (Y-90) based radioisotope pharmaceutical such as Y-90 ibritumomab-tiuxetan.

In various aspects, the radioisotope pharmaceutical is a Lu-177 based radioisotope pharmaceuticals, and the non-radioactive drug molecule precursor is a Lu-176 drug molecule precursor.

In various aspects, the radioisotope pharmaceutical is Lu-177 dotatate, and the non-radioactive drug molecule precursor is Lu-176 dotatate. In embodiments, the Lu-177 dotatate is produced by directly irradiating the Lu-176 dotatate using neutrons generated by the electronic neutron generator array.

In various aspects, the radioisotope pharmaceutical is the I-131 based radioisotope pharmaceutical, and the non-radioactive drug molecule precursor is a tellurium (Te) drug molecule precursor. In embodiments, the I-131 based radioisotope pharmaceutical is produced by directly irradiating the tellurium drug molecule precursor using neutrons generated by the electronic neutron generator array.

In various aspects, the radioisotope pharmaceutical is I-131 tositumomab, and the non-radioactive drug molecule precursor is tellurium tositumomab. In embodiments, the I-131 tositumomab is produced by directly irradiating the tellurium tositumomab using neutrons generated by the electronic neutron generator array.

In various aspects, the radioisotope pharmaceutical is the Y-90 based radioisotope pharmaceutical, and the non-radioactive drug molecule precursor is a yttrium-89 (Y-89) drug molecule precursor. In embodiments, the Y-90 based radioisotope pharmaceutical is produced by directly irradiating the Y-89 drug molecule precursor using neutrons generated by the electronic neutron generator array.

In various aspects, the radioisotope pharmaceutical is Y-90 ibritumomab-tiuxetan, and the non-radioactive drug molecule precursor is Y-89 ibritumomab-tiuxetan. In embodiments, the Y-90 ibritumomab-tiuxetan is produced by directly irradiating the Y-89 ibritumomab-tiuxetan using neutrons generated by the electronic neutron generator array.

In various aspects, the present disclosure provides a device for producing a Lu-177 based radioisotope pharmaceutical from an non-radioactive irradiation target material by irradiating the non-radioactive irradiation target material using neutrons generated by an electronic neutron generator array or other neutron emitting materials such as Californium-252 (Cf-252) sources.

In various aspects, the present disclosure provides a device for producing a Lu-177 based radioisotope pharmaceutical directly from a non-radioactive Lu-176 complex (or compound) by irradiating the non-radioactive Lu-176 complex or compound using neutrons generated by an electronic neutron generator array or other neutron emitting material such as Californium-252 (Cf-252) sources.

In various aspects, the irradiation target material comprises or is a non-radioactive Lu-176 mixture or Lu-176 complex precursor. In embodiments, the Lu-176 mixture comprises or is a reacted mixture of a Lu-176 complex and a target cell receptor binding moiety such as peptide linked to a chelating agent as discussed herein above and elsewhere in the present disclosure. In embodiments, the Lu-176 precursor comprises or is a complex of Lu-176 and a target cell receptor binding moiety linked to a chelating agent.

In various aspects, the target cell receptor binding moiety comprises or is a target cell receptor binding antibody (or antibody-derived fragment), peptide, protein, small molecule inhibitor, or DNA/RNA aptamer. In embodiments, the target cell receptor binding moiety comprises or is a target cell receptor binding peptide.

In various aspects, the irradiation target material comprises or is Lu-176 dotatate. In various aspects, the irradiation target material comprises or is a reacted mixture of a Lu-176 compound and dotatate.

In various aspects, the present disclosure provides a system for preparing a Lu-177 based radioisotope pharmaceutical. The system comprises a device including at least one electronic neutron generator, an irradiation module and an irradiation module insert; a target cooling unit; and a control unit. The device, the target cooling unit and the control unit are discussed herein above and elsewhere in the present disclosure.

The method and device of the present disclosure advantageously minimize the production cost and improves the handling safety through production of Lu-177 based radioisotope pharmaceuticals by directly irradiating non-radioactive drug molecule precursors without handling any radioactive intermediate compounds.

The method and device of the present disclosure allow direct production of radioisotope pharmaceuticals by directly irradiating non-radioactive drug molecule precursors to convert them to the final radioisotope pharmaceuticals without requiring the use of a nuclear reactor, which makes it possible to produce the radioactive cancer treatment drugs and radioisotope pharmaceuticals in an industrial or clinical setting, such as a hospital or cancer treatment center.

The method and device of the present disclosure allow the neutron energy spectrum to be controlled to maximize the desired neutron capture reactions in the irradiation target material.

The method and device of the present disclosure further advantageously include the ability to control the temperature of the irradiation target material in the irradiation chamber, using a coolant temperature and flow rate supply system, and thus can minimize chemical bond breakage in the drug molecules caused by thermal effects.

The method and device of the present disclosure advantageously use a combination of borated water composition and low-Z metallic radiation shielding such as aluminum, to minimize radiation exposure to the area surrounding the production device.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. All of the aspects and embodiments may be combined according to the present disclosure. It is to be expressly understood, however, that the drawings are for the purpose of illustration and description only and are not intended as a definition of the limits of the disclosure.

BRIEF DESCRIPTION OF THE DRAWINGS

Various features of the aspects described herein are set forth with particularity in the appended claims. The various aspects, however, both as to organization and methods of operation, together with advantages thereof, may be understood in accordance with the following description taken in conjunction with the accompanying drawings as follows:

FIG. 2A illustrates a radial cross section view of the irradiation device having an array of electronic neutron generators arranged at the same plane and configured to direct their neutrons toward the center of the Irradiation module insertion tube (Rabbit Hole) where the irradiation chamber is located when the irradiation module insert is inserted into the Irradiation module insertion tube; FIG. 2B illustrates an axial cross section view of the irradiation system with the irradiation module insert installed along the A-A section line in FIG. 2A; FIG. 2C illustrates an axial cross section view of the irradiation module insert; and FIG. 2D illustrates a radial cross section view of the irradiation module insert along the B-B section line in FIG. 2C.

FIG. 3A illustrates a radial cross section view of the irradiation device having an array of electronic neutron generators arranged at different planes and configured to direct their neutrons from different angles toward the center of the Irradiation module insertion tube where the irradiation chamber is located when the irradiation module insert is inserted into the Irradiation module insertion tube; FIG. 3B illustrates an axial cross section view of the irradiation system with the irradiation module insert installed along the A-A section line in FIG. 3A; FIG. 3C illustrates an axial cross section view of the irradiation module insert; and FIG. 3D illustrates an radial cross section view of the irradiation module insert along the B-B section line in FIG. 3C.

Figure 1:
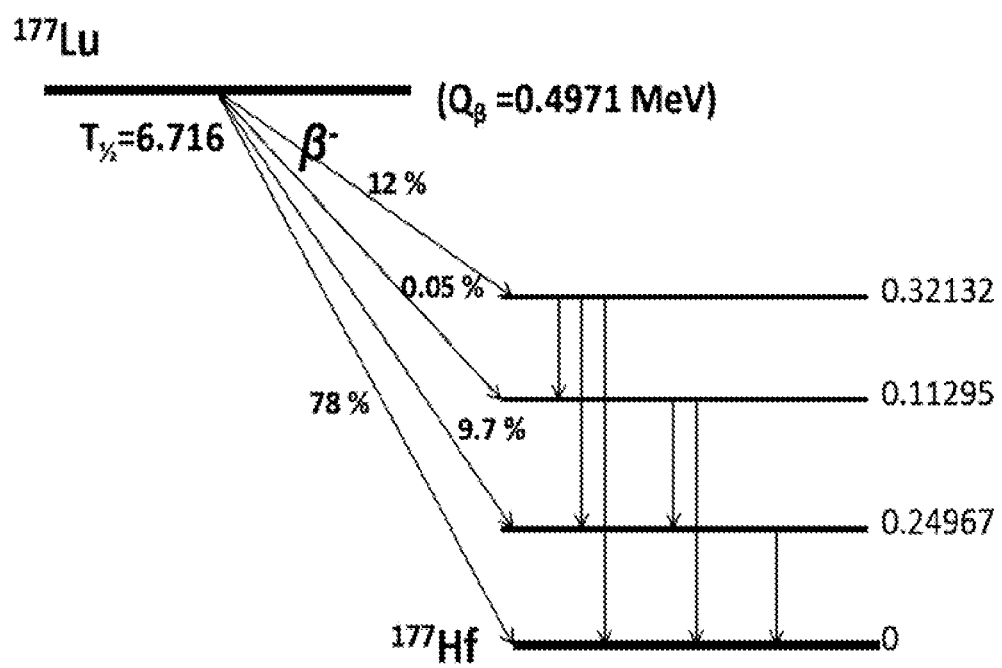
FIG. 1 illustrates a simplified decay scheme for Lu-177 ($^{177}$Lu).

The exemplifications set out herein illustrate various aspects of the disclosure, in one form, and such exemplifications are not to be construed as limiting the scope of the disclosure in any manner.

DETAILED DESCRIPTION

Before explaining various aspects of the articulated manipulator in detail, it should be noted that the illustrative examples are not limited in application or use to the details of disclosed in the accompanying drawings and description. It shall be appreciated that the illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof.

In various aspects, the present disclosure provides devices, systems and methods for direct production of a radioisotope-based cancer treatment pharmaceutical directly from a corresponding non-radioactive drug molecule precursor by irradiating the non-radioactive drug molecule precursor using neutrons generated by an electronic neutron generator array or other neutron emitting material such as Californium-252 (Cf-252) sources. The radioisotope pharmaceutical can be a radioisotope-based cancer treatment pharmaceuticals. Non-limiting examples of the radioisotope pharmaceutical include a Lu-177 based radioisotope pharmaceutical such as Lu-177 dotatate, an iodine-131 (I-131) based radioisotope pharmaceutical such as I-131 tositumomab, and a yttrium-90 (Y-90) based radioisotope pharmaceutical such as Y-90 ibritumomab-tiuxetan.

Different isotopes of a metal or metal ion have the same chemical properties. If a radioisotope pharmaceutical (radioisotope drug molecule) can be produced by a synthetic process, its corresponding non-radioactive isotope drug molecule precursor (non-radioactive drug molecule precursor) can be produced by the same synthetic process. In order to eliminate the need to handle and process radioisotope materials or radioisotope intermediate materials during the production of the radioisotope pharmaceutical to thus improve the production safety and reduce production cost and complexity, the present disclosure provides methods, devices and systems to prepare the non-radioactive isotope drug molecule precursor first and then to directly irradiate the non-radioactive isotope drug molecule precursor using neutrons produced by an electronic neutron generator array to produce the final radioisotope pharmaceutical.

A wide variety of radioisotope pharmaceuticals are increasingly used for cancer or tumor targeted treatments or imagining in clinics or hospitals.

Tumor targeting is a relatively novel but rapidly expanding technique applied for cancer treatment as well as visualization. Targeted drug delivery includes generally of tumor-targeting compounds (such as antibodies or antibody-derived fragments, proteins, peptides, small molecule inhibitors, or DNA/RNA aptamers) directing an attached drug such as a radionuclide to the tumor or cancer cells for localized cancer treatment or tumor visualization before or during surgery. The majority of these tumor-targeting compounds are directed against targetable cell membrane-bound proteins, such as anchoring proteins, receptors, enzymes and transporter proteins, overexpressed on the tumor or tumor-associated cells.

The present disclosure provides a targeted drug delivery based on targetable cell receptors which are overexpressed in the target cells (i.e., tumor or cancer cells) in contrast to the not-to-be-targeted cells such as normal cells. If a drug has a binding site to those overexpressed cell receptors, it allows the delivery of the drug after its administration in high concentration to those target cells while leaving other cells (such as normal cells), which are not of interested, unaffected. For example, if tumor cells are characterized by an overexpression of a specific cell receptor, a drug with binding affinity to the specific cell receptor will, after intravenous infusion, accumulate in high concentration in the tumor tissue while leaving the normal tissue unaffected.

This targeted drug delivery concept has also been applied to radioisotope pharmaceuticals to deliver radionuclides selectively to the target cells for diagnostic or therapeutic purposes. For this radioisotope pharmaceutical application, the target cell receptor binding moiety is typically linked to a chelating agent which is able to form a strong complex with the metal ions of a radionuclide. This radiopharmaceutical drug after administration is then delivered to the target cell and the decay of the radionuclide releases high energy electrons, positrons, alpha particles or beta particles as well as gamma rays at the target site for a localized treatment, which is usually referred as targeted radionuclide therapy (TRT).

A key advantage of TRT over other methods of radiotherapy is the ability to target deliver the therapeutic radionuclides directly to the tumor or target cells. This works because some tumours have overexpression of certain cell receptors, compared to normal tissue. A radionuclide can be combined with a target cell receptor binding moiety such as a peptide or its analogue which has binding affinity to the cell receptors so that it preferentially binds to the tumour. With a gamma emitter as the radionuclide, the technique can be used for imaging with a gamma camera or PET scanner to locate tumours. When paired with alpha or beta emitters, therapeutic effect can be achieved.

The TRT using a peptide as the target cell receptor binding moiety in radioisotope pharmaceuticals is also called peptide receptor radionuclide therapy (PRRT).

The lutetium-177 (Lu-177 or $^{177}$Lu) radionuclide has attracted considerable attention and exhibited great promise in the research, commercial and clinical communities for use in a variety of peptide receptor radionuclide therapy (PRRT) procedures. Lu-177 Dotatate (lutetium ($^{177}$Lu) oxodotreotide or Lutathera®) was approved by the FDA in early 2018 for treatment of gastroenteropancreatic neuroendocrine tumors (GEP-NETs).

Current methods for preparing Lu-177 based radioisotope pharmaceuticals require assembly of a molecule that incorporates the highly radioactive Lu-177 atoms during the production of the treatment drug vector, for example, Lu-177 dotatate. These methods typically include first preparing the radioisotope Lu-177 by irradiating a source material, for example by directly irradiating Lu-176 target via the reaction Lu-176(n,γ)Lu-177, or alternatively by indirectly irradiating Yb-176 target as in Yb-176(n,γ)Yb-177 which decays with a 1.9 hour half-life to Lu-177; separating the radioactive Lu-177 compound from the irradiated source material; preparing the radioactive Lu-177 reagent; mixing and reacting the radioactive Lu-177 reagent with a peptide and a chelating agent to form the Lu-177 based radioisotope pharmaceuticals.

One technical problem with the current preparation methods of Lu-177 based radioisotope pharmaceuticals is that the need to first prepare and then separate the radioisotope Lu-177 intermediate compounds from the irradiated source material and the need to handle the radioactive Lu-177 intermediate compounds during the production of the final drug products. The currently existing production methods have caused great safety concerns and further added significant expense to the cancer treatment process that make the application of the treatment to many patients in need thereof problematic if not impossible.

Furthermore, the radioisotope Lu-177 has a short half-life of about 6.65 days and the decay of the radioisotope Lu-177 to its non-radioactive form occurs constantly during the handling of Lu-177 and the production of the final drug products. This decay of the Lu-177 may lead to a decrease in its efficiency in delivering the therapeutic effects. The poor stability of the radioisotope Lu-177 and its lack of significant shelf-life require that the final Lu-177 radioisotope pharmaceutical products have so far to be manufactured as an individual patient's dose unit in the laboratories at the hospital and administered immediately to the patient who had to be present at that hospital already awaiting the PRRT.

A simplified decay scheme for Lu-177 ($^{177}$Lu) is shown in FIG. 1. The radioisotope Lu-177 decays in 76% of events ($E_{\beta(max)}$=0.497 MeV) to the stable ground state of $^{177}$Hf with a half-life of 6.65 days, and decays in 9.7% of events ($E_{\beta(max)}$=0.384 MeV) and 12% of the time ($E_{\beta(max)}$=0.176 MeV) to an excited state of $^{177}$Hf that lies 0.24967 MeV and 0.32132 MeV, respectively, above the ground state, which de-excites to the ground state with the photon emission. During these radioactive decay events, $^{177}$Lu emits β$^-$ particles with an $E_{\beta(max)}$ of 497 keV (78.6%), 384 keV (9.1%) and 176 keV (12.2%) and low-energy gamma photons [$E_\gamma$=113 keV (6.6%), 208 keV (11%)].

Therefore, there is a need of an improved method and system for producing radioisotope pharmaceuticals, for example, Lu-177 based radioisotope pharmaceuticals, that addresses one or more of the challenges of the conventional production methods discussed above.

The present disclosure provides improved methods, devices and systems for preparing the radioisotope pharmaceuticals which allow the desired radioisotope to be produced directly in the drug vector's final form from a non-radioactive compound precursor without any radioactive intermediate compounds using neutrons generated by an electronic neutron generator.

An electronic neutron generator is disclosed by Heibel et al. in U.S. Provisional Application No. 63/166,718, entitled, "PRODUCTION OF HIGH ENERGY GAMMA RADIATION USING AN ELECTRONIC NEUTRON GENERATOR FOR FOOD AND MEDICAL DEVICE STERILIZATION", the entire contents of which are incorporated herein by reference for all purposes.

An electronic neutron generator is also disclosed by Firestone et al. in U.S. Pat. No. 8,737,570, which is herein incorporated by reference in its entirety for all purposes.

The radioisotope pharmaceuticals used in peptide receptor radionuclide therapy (PRRT) of the present disclosure are constructed with three components: a radionuclide (such as Lu-177) which delivers the actual therapeutic effect; a target cell receptor binding moiety (such as a peptide or its analogue) that binds to the cell receptors overexpressed on the tumor or target cells; and a chelator (chelating agent) that is the essential link between the radionuclide and the target cell receptor binding moiety. The chelating agent is able to form a strong complex with the metal ions of the radionuclide; and link to the target cell receptor binding moiety to form the target cell receptor binding moiety linked to the chelating agent.

In embodiments, the radionuclide is Lu-177, I-131 or Yttrium-90 (Y-90, or $^{90}$) In embodiments, the radionuclide is Lu-177.

In embodiments, the target cell receptor binding moiety is selected from the group consisting of an antibody (or antibody-derived fragment), a peptide, a protein, a small molecule inhibitor, or a DNA/RNA aptamer.

In embodiments, the target cell receptor binding moiety is a target cell receptor binding peptide.

In embodiments, the target cell receptor binding peptide is a somatostatin receptor binding peptide. In embodiments, the somatostatin receptor binding peptide is selected from octreotide, octreotate, lanreotide, vapreotide and pasireotide, preferably selected from octreotide and octreotate.

In embodiments, the somatostatin receptor binding peptide is oxodotreotide.

In embodiments, the chelating agent is selected from the group consisting of DOTA, DTPA, NT, EDTA, DO3A, NOC and NOTA, preferably is DOTA.

In embodiments, the chelating agent is DOTA which forms strong complex with Lu-177 or Lu-176. DOTA is an organic compound with the formula $(CH_2CH_2NCH_2CO_2H)_4$ and has a chemical structure of Formula I as shown below.

Formula I

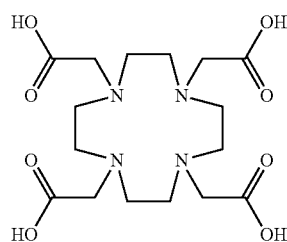

In embodiments, the target cell receptor binding moiety linked to the chelating agent is the somatostatin receptor binding peptide linked to the chelating agent DOTA, preferably DOTA-TATE (dotatate or oxodotreotide) or DOTA-TOC (dotatoc or edotreotide), more preferably DOTA-TATE (dotatate or oxodotreotide).

As used herein, the term "dotatate", "DOTA-TATE", "DOTATATE" or oxodotreotide shall refer to a somatostatin receptor binding peptide octreotate (an eight amino acid long peptide) linked to the bifunctional chelating agent DOTA. Dotatate has a chemical structure of Formula II as shown below.

Formula II

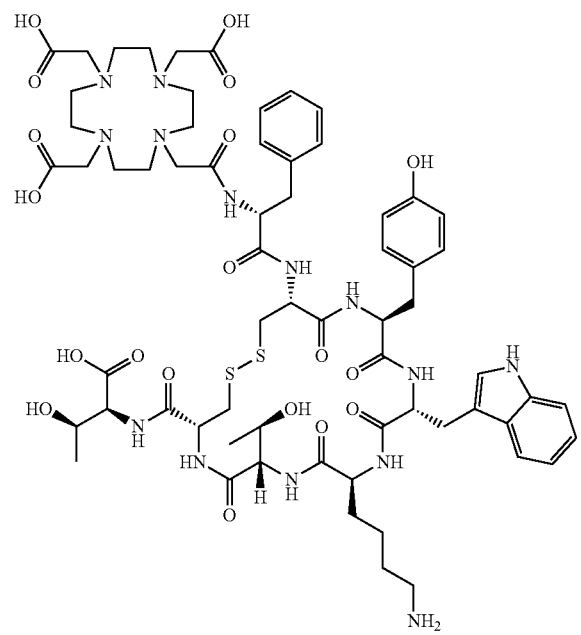

In embodiments, the radioisotope pharmaceutical comprises or is Lu-177 dotatate. The chemical structure of Lu-177 dotatate is illustrated as Formula III below.

Formula III

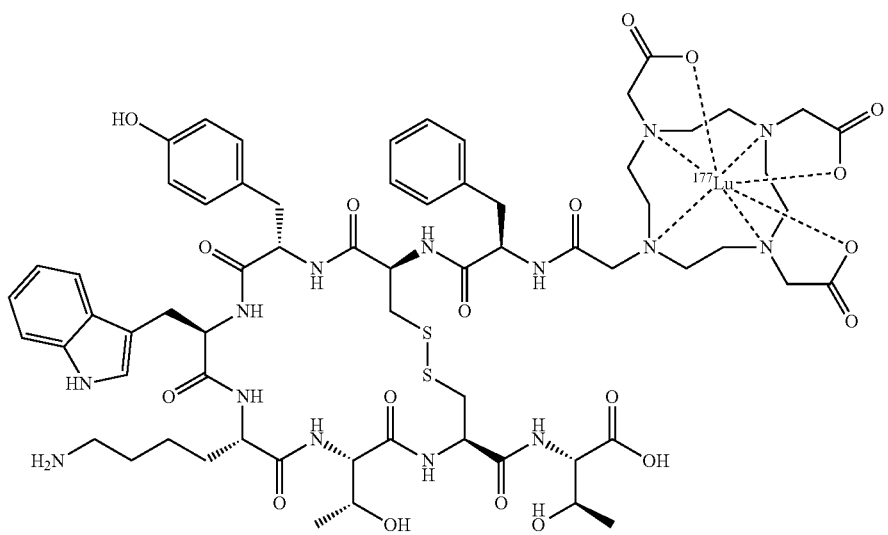

In embodiments, the non-radioactive Lu-176 drug precursor comprises or is Lu-177 dotatate. The Lu-176 dotatate may have or include a chemical structure illustrated as Formula IV below.

Formula Iv

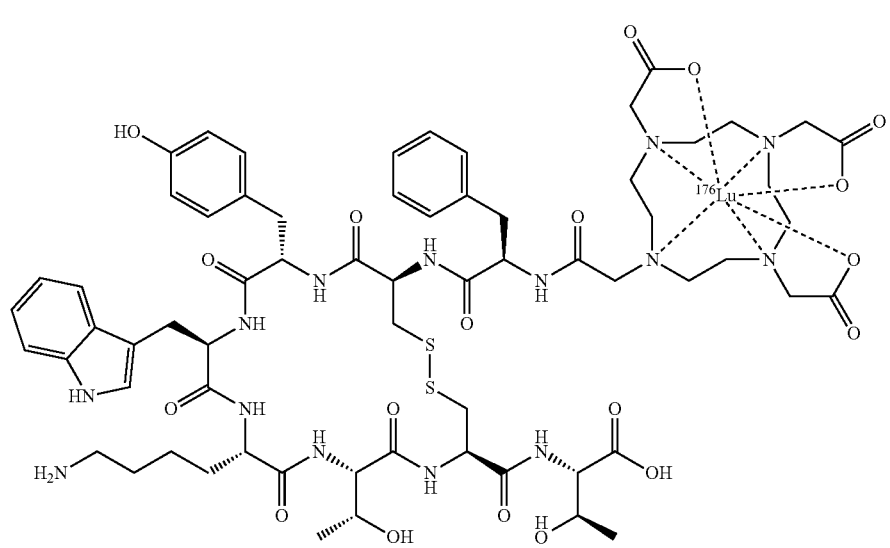

The present disclosure provides a method for preparing a Lu-177 based radiopharmaceutical using a non-radioactive Lu-176 drug precursor and thus to eliminate the need to separate the radioactive Lu-177 isotope from the irradiated source material and to eliminate the need to handle any radioactive Lu-177 intermediate compounds during the production of the Lu-177 based radiopharmaceutical. The method comprises preparing a non-radioactive reacted mixture of a Lu-176 compound, a peptide and a chelating agent; or a non-radioactive drug molecule precursor containing Lu-176; and irradiating the non-radioactive reacted mixture or the non-radioactive drug molecule precursor to convert at least part of the Lu-176 in the reacted mixture or drug molecule precursor to Lu-177 to form the final Lu-177 based radiopharmaceutical products. The method of the present disclosure thus eliminates the formation and handling of any Lu-177 intermediate compounds during the production of the final Lu-177 based radiopharmaceutical.

In embodiments, the Lu-177 based radioisotope pharmaceutical comprises or is Lu-77 dotatate. The method for preparing Lu-177 dotatate may include preparing a non-radioactive reacted mixture of Lu-176 and dotatate or a non-radioactive drug molecule precursor Lu-176 dotatate; and irradiating the reacted mixture or the drug molecule precursor Lu-176 dotatate to form the Lu-177 dotatate final products.

Different isotopes of a metal or metal ion have the same chemical properties. If a radioisotope pharmaceutical (radioisotope drug molecule) can be produced by a synthetic process, its corresponding non-radioactive isotope drug molecule precursor (non-radioactive drug molecule precursor) can be produced by the same synthetic process. In order to eliminate the need to handle and process radioisotope materials or radioisotope intermediate materials during the production of the radioisotope pharmaceutical to thus improve the production safety and reduce production cost and complexity, the present disclosure provides methods, devices and systems to prepare the non-radioactive isotope drug molecule precursor first and then to directly irradiate the non-radioactive isotope drug molecule precursor using neutrons produced by an electronic neutron generator array to produce the final radioisotope pharmaceutical.

A method for producing a Lu-177 based radioisotope pharmaceutical (such as Lu-177 dotatate) from Lu-177 is disclosed in U.S. Pat. Nos. 10,596,276 and 10,596,278 (the '276 and '278 patents), the entire contents of which are incorporated herein by references for all purposes.

Because the non-radioactive Lu-176 isotope has the same chemical properties and reactivity as those of Lu-177 radioisotope, the corresponding Lu-176 drug molecule precursor such as Lu-176 dotatate can be produced by a method similar to the methods disclosed in the '276 and '278 patents.

The method advantageously allows the drug molecules to be created using the non-radioactive isotope Lu-176 and thus eliminates the need to prepare the radioisotope Lu-177, separate the radioisotope Lu-177 from the irradiated source material, and handle of the radioisotope Lu-177 during the production of the Lu-177 based radiopharmaceutical in its final form.

In various aspects, one or more of the present methods are designed to ensure that the non-radioactive drug molecule precursor may be prepared first and then directly irradiated with thermal and epithermal neutrons to form the drug vector molecules (the final radioisotope pharmaceutical) in an environment where the temperature and gamma radiation levels can be controlled to ensure there is minimal decomposition of the drug vector molecules due to thermal or gamma radiation induced chemical bond breakage in the molecules. This approach may be used to produce a number of other radiopharmaceutical drugs using non-radioactive isotopes to be converted through neutron irradiation to the radioisotope desired to be included into the drug vector molecules. Other applications of the process described herein include the production of radioactive tracers for material property condition monitoring, such as Na-24, and medical therapeutic and diagnostic imaging material creation such as Cu-64, Ho-166, P-32, and K-42.

In embodiments, the method for producing a Lu-177 radioisotope pharmaceutical comprises: forming a complex (the drug molecule precursor) of the non-radioactive Lu-176 and a target cell receptor binding peptide linked to a chelating agent by: 1) providing an aqueous solution comprising the non-radioactive Lu-176; 2) providing an aqueous solution comprising the target cell receptor binding peptide linked to the chelating agent; 3) mixing the aqueous solutions provided in steps 1) and 2) to form a resulted mixture; and 4) heating the resulted mixture to form a solution comprising the complex (the drug molecule precursor).

In embodiments, the method may further comprise: 5) drying the solution comprising the complex to form an irradiation source/target material which is a solid or concentrate comprising the complex; and 6) irradiating the irradiation source/target material comprising the complex to covert at least a portion of the Lu-176 to Lu-177 to form the final drug Lu-177 radioisotope pharmaceutical.

In embodiments, the method may further comprise adding a stabilizer against radiolysis or radiolytic degradation such, the stabilizer being selected from gentisic acid or a salt thereof, ascorbic acid or a salt thereof, or ethanol. In embodiments, the stabilizer is selected from gentisic acid or a salt thereof, or ascorbic acid or a salt thereof.

In embodiments, the method may exclude addition of any stabilizer such as acids or their salts (i.e., gentisic or ascorbic acids or a salt thereof) or alcohol (i.e., ethanol).

In embodiments, the irradiation source/target material is a solid comprising the complex.

In embodiments, the irradiation source/target material is a concentrate comprising the complex.

In embodiments, the method may optionally further comprise purifying the irradiation source/target material to obtain a purified irradiation source/target material before the irradiation in step 6).

In embodiments, the chelating agent comprises or is selected from the group consisting of DOTA, DTPA, NT, EDTA, DO3A, NOC and NOTA, and preferably DOTA.

In embodiments, the target cell receptor binding peptide comprises or is a somatostatin receptor binding peptide. In embodiments, the somatostatin receptor binding peptide is selected from octreotide, octreotate, lanreotide, vapreotide and pasireotide, preferably selected from octreotide and octreotate. In embodiments, the somatostatin receptor binding peptide is oxodotreotide.

In embodiments, the target cell receptor binding peptide linked to the chelating agent comprises or is selected from the group consisting of DOTA-OC, DOTA-TOC (edotreotide), DOTA-NOC, DOTA-TATE (oxodotreotide), DOTA-LAN, and DOTA-VAP.

In embodiments, the target cell receptor binding peptide linked to the chelating agent comprises or is preferably DOTA-TATE (oxodotreotide) or DOTA-TOC (edotreotide), more preferably DOTA-TATE (oxodotreotide).

In embodiments, the complex comprises or is Lu-176 dotatoc or Lu-176 dotatate (the drug precursor), preferably Lu-176 dotatate.

In embodiments, the final drug Lu-177 radioisotope pharmaceutical comprises or is Lu-177 dotatoc or Lu-177 dotatate (the final drug), preferably Lu-177 dotatate.

As used herein, the chelating agent in the context of the present disclosure may be DOTA which is 1,4,7,10-Tetraazacyclododecane-1,4,7,10-tetraacetic acid; DTPA which is Diethylentriaminepentaacetic acid; NTA which is Nitrilotriacetic acid; EDTA which is Ethylenediaminetetraacetic acid; DO3A which is 1,4,7,10-Tetraazacyclododecane-1,4, 7-triacetic acid; NOTA which is 1,4,7-Triazacyclononane-1,4,7-triacetic acid; Trizoxetan; Tetraxetan or mixtures thereof, preferably is DOTA.

As used herein, the term "target cell receptor binding moiety" shall refer to a chemical molecule which binds with at least part of its molecule to a receptor molecule at the surface of a target cell such as tumor or its associated cells. A cell receptor binding moiety, for which the present disclosure is in particular suitable, is a somatostatin receptor binding peptide, preferably the somatostatin receptor binding peptide is selected from octreotide, octreotate, lanreotide, vapreotide, pasireotide, ilatreotide, pentetreotide, depreotide, satoreotide, veldoreotide, preferably selected from octreotide and octreotate.

As used herein, the term "linked" shall refer to the cell receptor binding moiety is either directly linked to the chelating agent or connected via a linker molecule, preferably it is directly linked. The linking bond(s) is (are) either covalent or non-covalent bond(s) between the cell receptor binding moiety (and the linker) and the chelating agent, preferably the bond(s) is (are) covalent.

The present disclosure provides a device for producing radioisotope pharmaceuticals, for example, the Lu-177, I-131 and Y-90 based radioisotope pharmaceuticals. In various embodiments, as shown schematically in FIGS. 2A to 2D, the device 200 comprises an array of electronic neutron generators 202 (7 electronic neutron generators in this embodiment) to generate neutrons or a thermal neutron flux; an irradiation module 250; and an irradiation module insert 216.

In embodiments, the device 200 may further comprise a target cooling unit 212 configured to attach to the irradiation module 250 to control the temperature of at least a portion of the irradiation module 250. In embodiments, the target cooling unit 212 includes a liquid coolant which can be circulated through at least a portion of the irradiation module 250 and thus to control the temperature of at least a portion of the irradiation module 250.

In embodiments, the device 200 may further comprise a control unit attached to the irradiation module 250 and the irradiation module insert 216. In embodiments, the control unit can be a control circuit. The control circuit may comprise a controller comprising one or more processors (e.g., microprocessor, microcontroller) coupled to at least one memory circuit. The memory circuit stores machine executable instructions that when executed by the processor, cause the processor to execute machine instructions to implement various processes described herein. The processor may be any one of a number of single or multi-core processors known in the art. The memory circuit may comprise volatile and non-volatile storage media. The processor may include an instruction processing unit and an arithmetic unit. The instruction processing unit may be configured to receive instructions from the memory circuit.

In embodiments, the irradiation module 250 comprises an irradiation module insertion tube (Rabbit Hole) 210; a heavy water ($D_2O$) moderator module 208 with adjustable thickness surrounding and attached to the outer side surface of the Irradiation module insertion tube 210; a borated water module 206 surrounding and attached to the outer side surface of the $D_2O$ moderator module 208; and a metallic shielding module 204 surrounding and attached to the outer surface of the borated water module 206. In embodiments, the irradiation module insertion tube 210 has an insertion port 214 for placing the irradiation module insert 216 into the Irradiation module insertion tube 210.

Figure 2A:
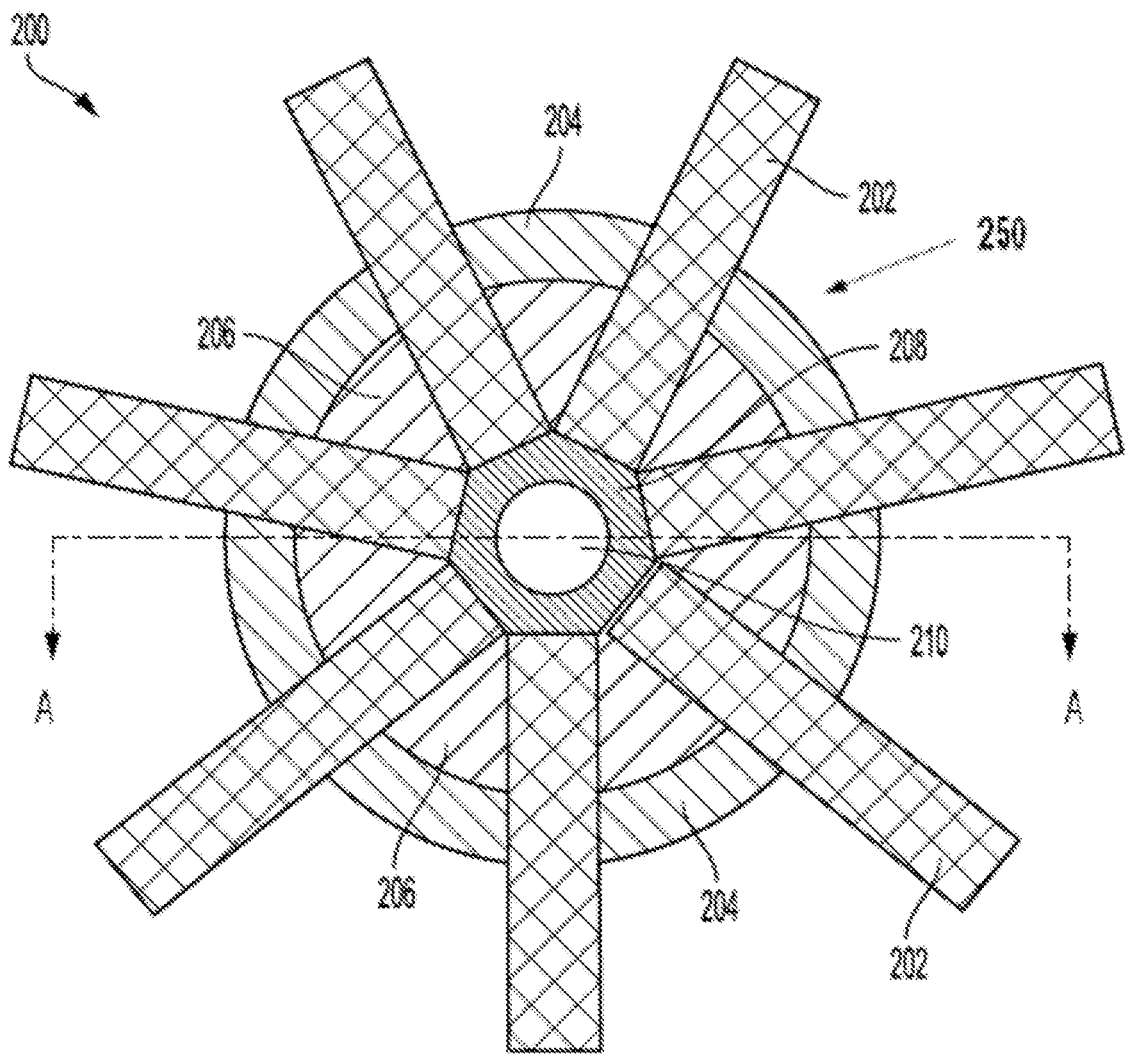
FIGS. 2A to 2D illustrate a schematic representation of a system for preparing radioisotope pharmaceuticals from non-radioactive drug molecule precursor.
Figure 2B:
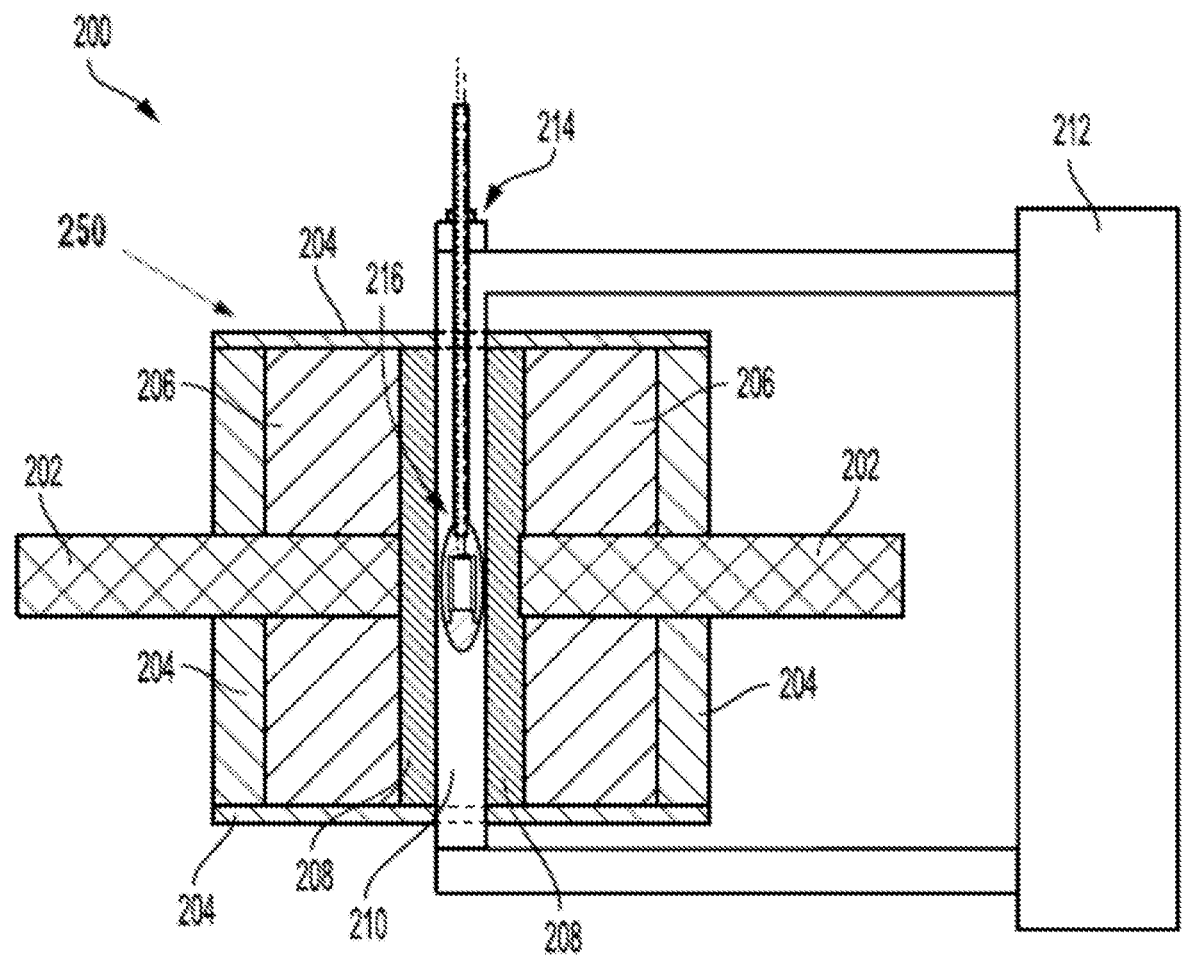

In embodiments, as shown in FIGS. 2A and 2B, the array of electronic neutron generators 202 are configured to be in a same plane and direct its neutrons or thermal neutron flux to the center (the middle section) of the irradiation module insertion tube of the irradiation module 250.

Figure 2C:
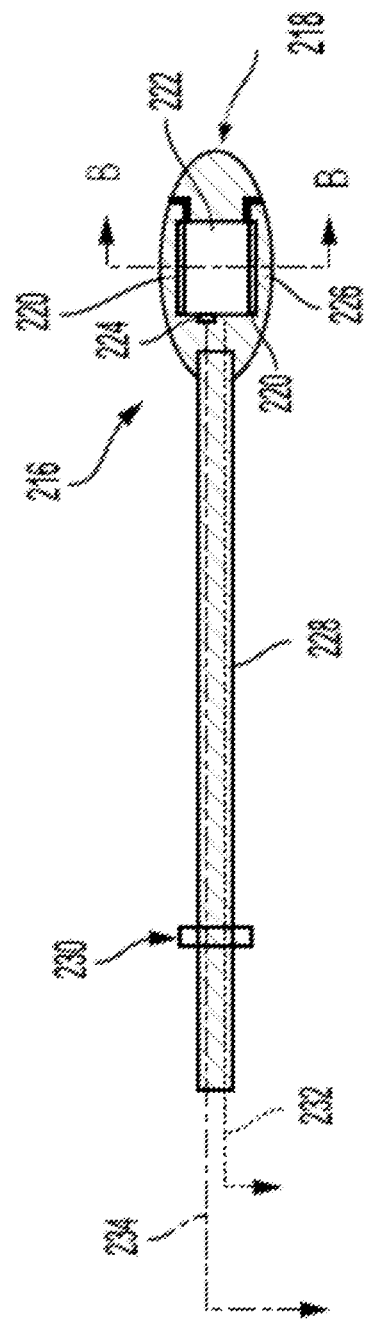

In embodiments, as shown in FIG. 2C, the irradiation module insert 216 comprises an insertion rod 228; a removable nose 218 configured to detachably connect to the insertion rod 228; an irradiation chamber 222 housed in the removable nose 218; an insertion position lock ring 230 configured to attach to the insertion rod 228 for locking irradiation module insert 216 with the insertion port 214 to adjust the position of the irradiation chamber 222 inside the Irradiation module insertion tube 210; a radiation detector 220 surrounding and/or attached to the irradiation chamber 222 for detecting the irradiation level from the irradiation chamber 222; and a temperature sensor 224 coupled to the irradiation chamber 222 for sensing the temperature of the irradiation chamber 222.

In embodiments, the irradiation module insert 216 further comprises an irradiation detector signal output 232 configured to deliver the detected irradiation signal from the radiation detector 220 to the control unit, and a temperature sensor signal output 234 configured to deliver the sensed temperature signal from the temperature sensor 224 to the control unit. In certain embodiments, output signals of the radiation detector 220 and/or the temperature sensor 224 can be communicated wirelessly to the control unit using any suitable wireless communication protocol.

As shown in FIG. 2B, the irradiation module insert 216 is configured to be placed into the Irradiation module insertion tube 210 and keep the irradiation chamber 222 at substantially the center or middle section of the Irradiation module insertion tube 210 and also at the center of the array of electronic neutron generators 202 so that the neutron radiation from the electronic neutron generators 202 are all directed to the irradiation chamber 222.

In embodiments, the irradiation module insert 216 is configured to allow the irradiation target material to be placed into the irradiation chamber 222 housed inside the removable nose 218.

Figure 2D:
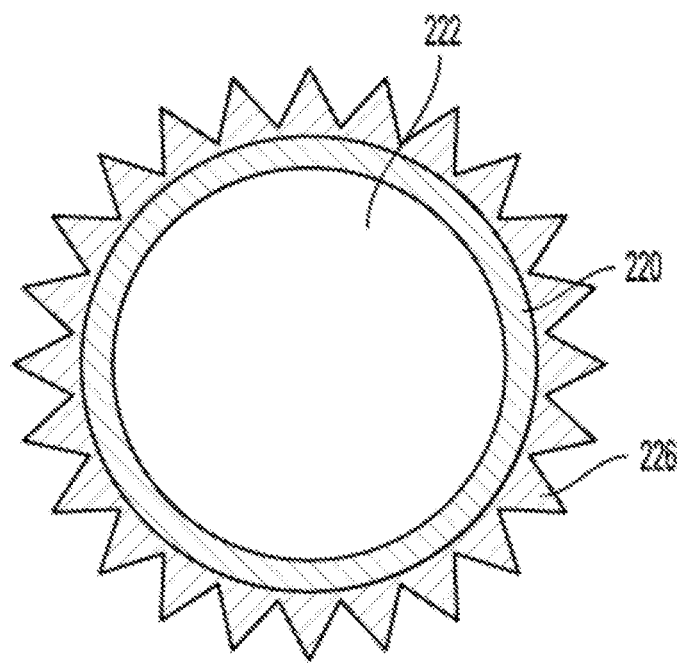

FIG. 2D illustrates a radial cross section view of the radiation detector 220 along the section line B-B in FIG. 2C. In embodiments, as shown in FIG. 2D, the irradiation chamber 222 is a hollow cylinder for housing an irradiation source (or target) material, and the irradiation detector 220 is a hollow cylinder concentric with the irradiation chamber 222 and is configured to surround and/or attach to at least a portion or the entire outer side (curved) surface of the irradiation chamber 222, preferably the entire outer side surface of the irradiation chamber 222. The irradiation detector 220 may or may not cover the top and bottom round surfaces of the irradiation chamber 222.

In embodiments, as shown in FIG. 2B, the target cooling unit 212 is configured to circulate the coolant through the Irradiation module insertion tube 210 so to control the temperatures inside the Irradiation module insertion tube 210 and thus the temperature of the irradiation chamber 222.

In embodiments, the device comprises the control unit (not shown) configured to: 1) receive the detected irradiation level signal from the cylindrical radiation detector 220 and the sensed temperature signal from the temperature sensor 224; 2) adjust parameters of the target cooling unit 212 to control the temperature inside the Irradiation module insertion tube 210 and also the irradiation chamber 222 to be maintained in predetermined temperature range; 3) determine whether the detected irradiation level reaches a predetermined level; and 4) turn off the array of the electronic neutron generators when the detected irradiation level reaches the predetermined level.

In embodiments, the device does not include the target cooling unit 212 and does not include the control unit. In embodiments, the device is configured to connect to an external target cooling unit 212 and/or an external control unit.

In embodiments, the irradiation target material comprises or is a non-radioactive Lu-176 mixture or a non-radioactive Lu-176 drug molecule precursor. In embodiments, the irradiation target material comprises or is Lu-176 dotatate. In embodiments, the irradiation target material comprises or is a reacted mixture of Lu-176 and dotatate.

FIGS. 2A and 2B illustrate a system for preparing a radioisotope pharmaceutical, such as Lu-177, I-131, Y-90 and other radioisotopes based pharmaceuticals. The system comprises a device including at least one electronic neutron generator 202 (7 electronic neutron generators in this embodiment); an irradiation module 250; and an irradiation module insert 216, as discussed herein above. The system further comprises a target cooling unit 212. The system further comprises a control unit (not shown).

The use of an array of electronic neutron generators 202 configured as shown schematically in FIGS. 2A to 2D will allow containers with either solid or concentrated liquid forms of the drug precursor or other application molecules to be placed in the irradiation chamber 222 to be irradiated in a neutron flux field that has a neutron energy distribution that may be optimized for the neutron absorption resonances in the target material, such as a Lu-177 based drug, by adjusting the thickness of the moderator module housing the deuterium oxide ($D_2O$) and thus the thickness of a moderating material $D_2O$, positioned in the area between the neutron generators and the Irradiation module insertion tube shown in FIGS. 2A and 2B. Since these are typically very low energy neutrons, there will be minimal interactions between the chemical bonds and the neutrons that damage the structure of the molecules.

For direct production of a drug such as Lu-177 dotatate, the large neutron capture cross section of Lu-176, and very low neutron capture cross sections of the other materials in the drug molecule, ensures a relatively high amount of Lu-177 production. The temperature of the irradiation target material comprising the non-radioactive drug molecule precursor can be controlled by controlling the rate and temperature of the coolant flowing around the irradiation module insert 216 having the irradiation chamber 222 housing the irradiation target/source material as shown schematically in FIG. 2B. The activity of the desired radioisotope contained within the irradiation target material can be determined easily by those skilled in the art by measurement of the intensity of the gamma or X-ray radiation emitted by the irradiation target material when the neutron capture occurs using radiation detection equipment configured as shown in FIGS. 2C and 2D. When the measured material activity reaches the desired predetermined level (e.g., saturation equilibrium), the neutron generators 202 can be simply turned off and the resulted irradiated target material, such as the resulted final Lu-177 drug comprising or being Lu-177 dotatate, can be removed from the irradiation module 250, like the one shown in FIGS. 2B and 2C, and used directly without the need for further processing.

FIGS. 3A-3D illustrate a device 300 for preparing a Lu-177 based radioisotope pharmaceutical which is similar to the device as shown in FIGS. 2A-2D. The device 300 comprises: at least one electronic neutron generator 302 (10 electronic neutron generators in this embodiment); an irradiation module 350; and an irradiation module insert 316. The device 300 further comprises a target cooling unit 312.

The device 300 further comprises a control unit. In embodiments, the control unit can be a control circuit. The control circuit may comprise a controller comprising one or more processors (e.g., microprocessor, microcontroller) coupled to at least one memory circuit. The memory circuit stores machine executable instructions that when executed by the processor, cause the processor to execute machine instructions to implement various processes described herein. The processor may be any one of a number of single or multi-core processors known in the art. The memory circuit may comprise volatile and non-volatile storage media. The processor may include an instruction processing unit and an arithmetic unit. The instruction processing unit may be configured to receive instructions from the memory circuit.

Figure 3A:
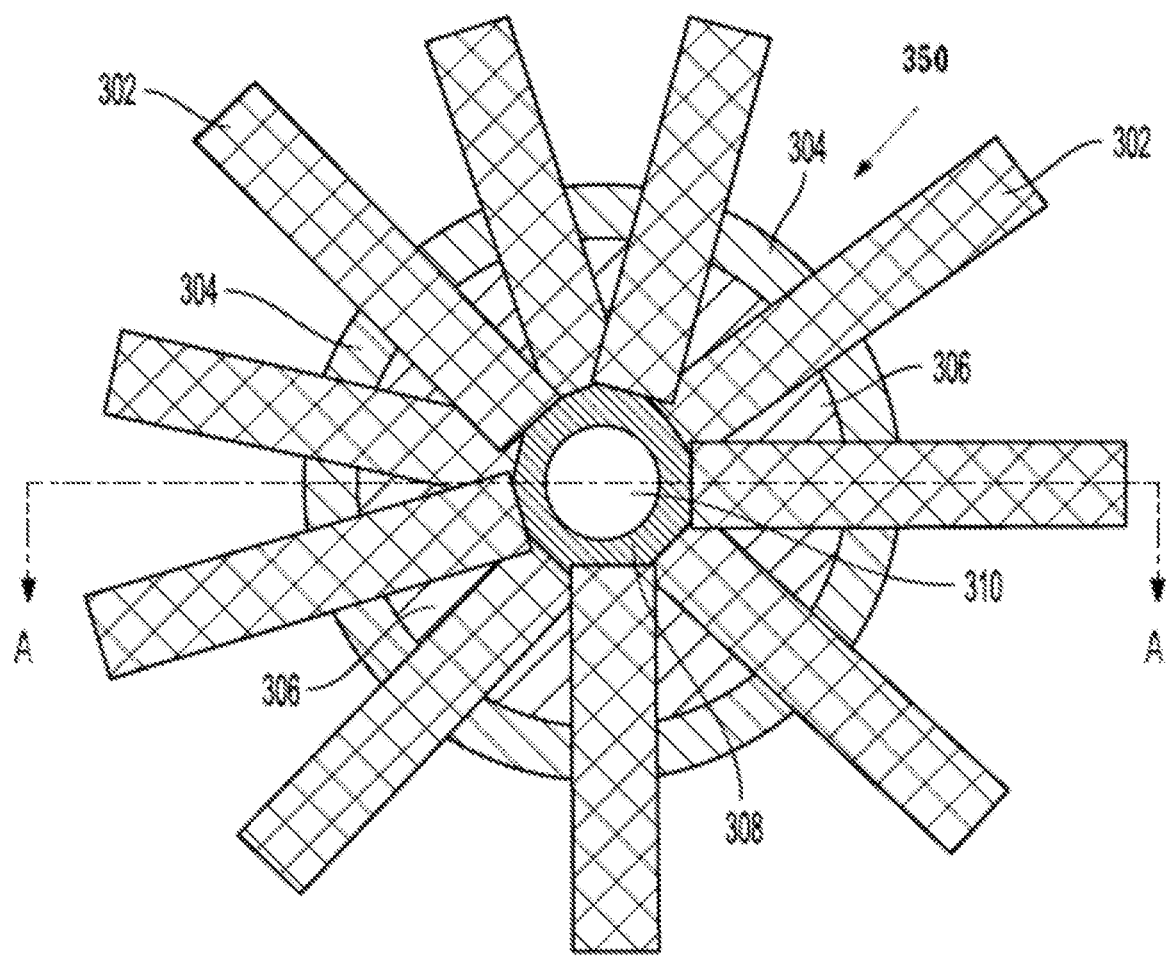
FIGS. 3A to 3D illustrate a schematic representation of a system for preparing radioisotope pharmaceuticals from non-radioactive drug molecule precursor.
Figure 3B:
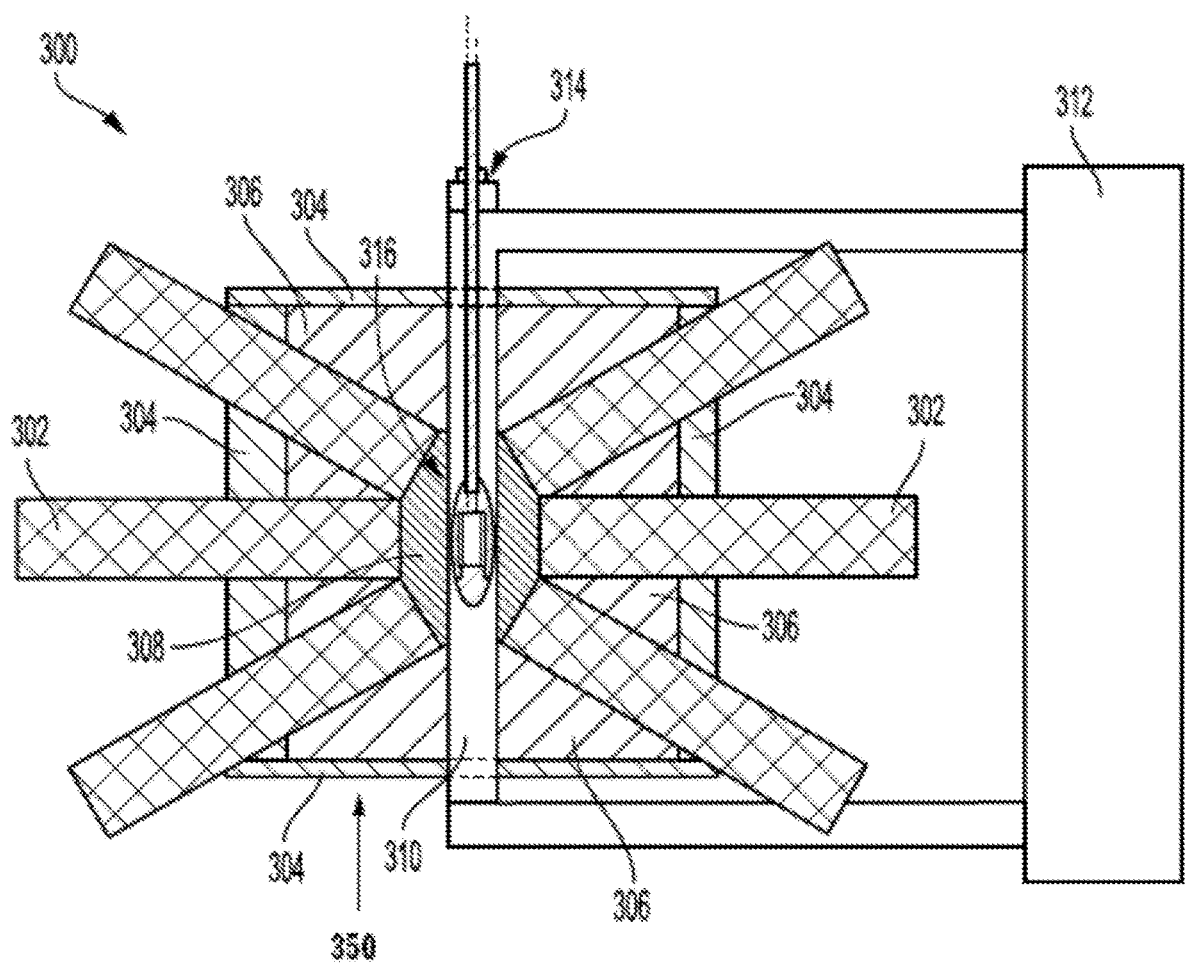

In embodiments, the device 300 is configured to have part of the electronic neutron generators 302 in this embodiment to be placed in a same first plane and the rest of the electronic neutron generators to be placed at different angles such as at 45° from the first plane as shown in FIG. 3B. All the electronic neutron generators 302 are configured to direct their neutron radiation or thermal neutron flux to the center (middle section) of the Irradiation module insertion tube 310 so that the irradiation target material in irradiation chamber 322 of the irradiation module insert 316 when inserted in the Irradiation module insertion tube 310 can be irradiated by the neutron flux from different angles as shown in FIG. 3B. All the other components of device 300 are the same as those of device 200 discussed above and are described briefly below.

In embodiments, the irradiation module 350 comprises an irradiation module insertion tube (Rabbit Hole) 310; a heavy water ($D_2O$) moderator module 308 with adjustable thickness surrounding and attached to the outer side surface of the irradiation module insertion tube 310; a borated water module 306 surrounding and attached to the outer side surface of the $D_2O$ moderator module 308; and a metallic shielding module 304 surrounding and attached to the outer surface of the borated water module 306. In embodiments, the irradiation module insertion tube (Rabbit Hole) 310 has an insertion port 314 for placing the irradiation module insert 316 into the Irradiation module insertion tube 310.

Figure 3C:
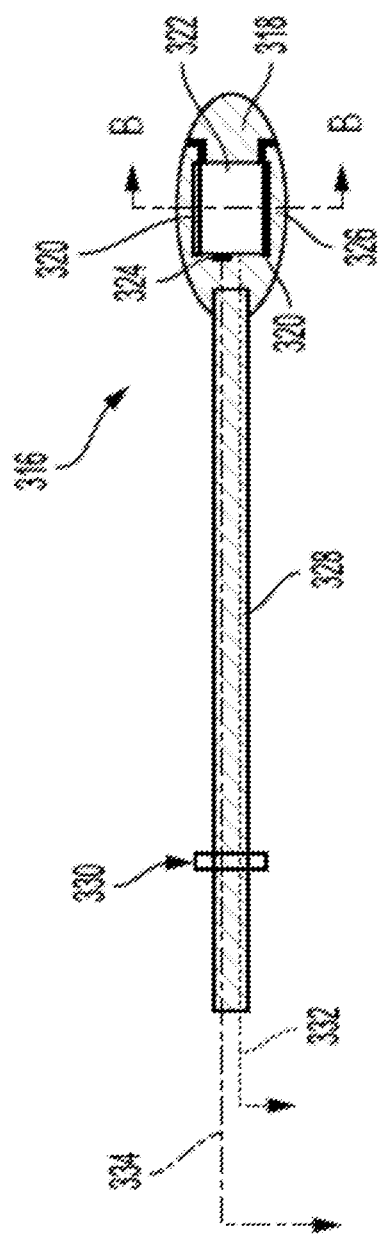
Figure 3D:
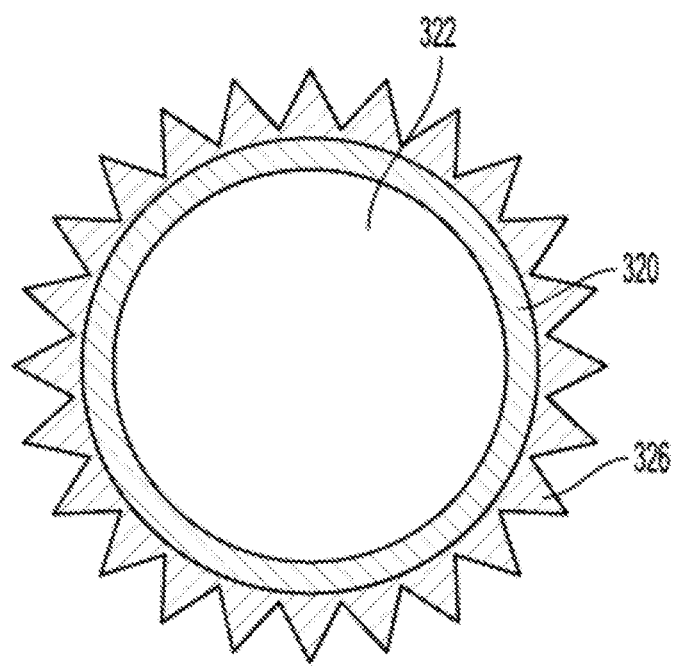

As shown in FIG. 3C, the irradiation module insert 316 comprises an insertion rod 328; a removable nose 318 configured to detachably connect to the insertion rod 328; an irradiation chamber 322 housed in the removable nose 318; an insertion position lock ring 330 configured to attach to the insertion rod 328 for locking irradiation module insert 316 with the insertion port 314 to adjust the position of the irradiation chamber 322 inside the Irradiation module insertion tube 310; a radiation detector 320 surrounding and/or attached to the irradiation chamber 322 for detecting the irradiation level from the irradiation chamber 322; and a temperature sensor 324 coupled to the irradiation chamber 322 for sensing the temperature of the irradiation chamber.

In embodiments, as shown in FIG. 3C, the irradiation module insert 316 further comprises an irradiation detector signal output 332 configured to deliver the detected irradiation signal from the radiation detector 320 to the control unit (not shown), and a temperature sensor signal output 334 configured to deliver the sensed temperature signal from the temperature sensor 324 to the control unit.

In embodiments, the borated water module 206 in FIGS. 2A-2D and 306 in FIGS. 3A-3D comprises a borated water composition including 8-12 wt. % of sodium borate, 8-20 wt. % or more than 20 wt. % of boric acid, and balance water. One of the advantages of using borated water is that the water enriched with borate can achieve the same shielding effects at reduced water volume as compared to normal water.

In various aspects, the method and device of the present disclosure advantageously use a combination of borated water composition and low-Z metallic radiation shielding such as aluminum, to minimize radiation exposure to the area surrounding the production device. Borated water is used as a coolant during normal operation of pressurized water reactors (PWRs) as well as in Emergency Core Cooling Systems (ECCS) of both PWRs and boiling water reactors (BWRs).

Figure 4:
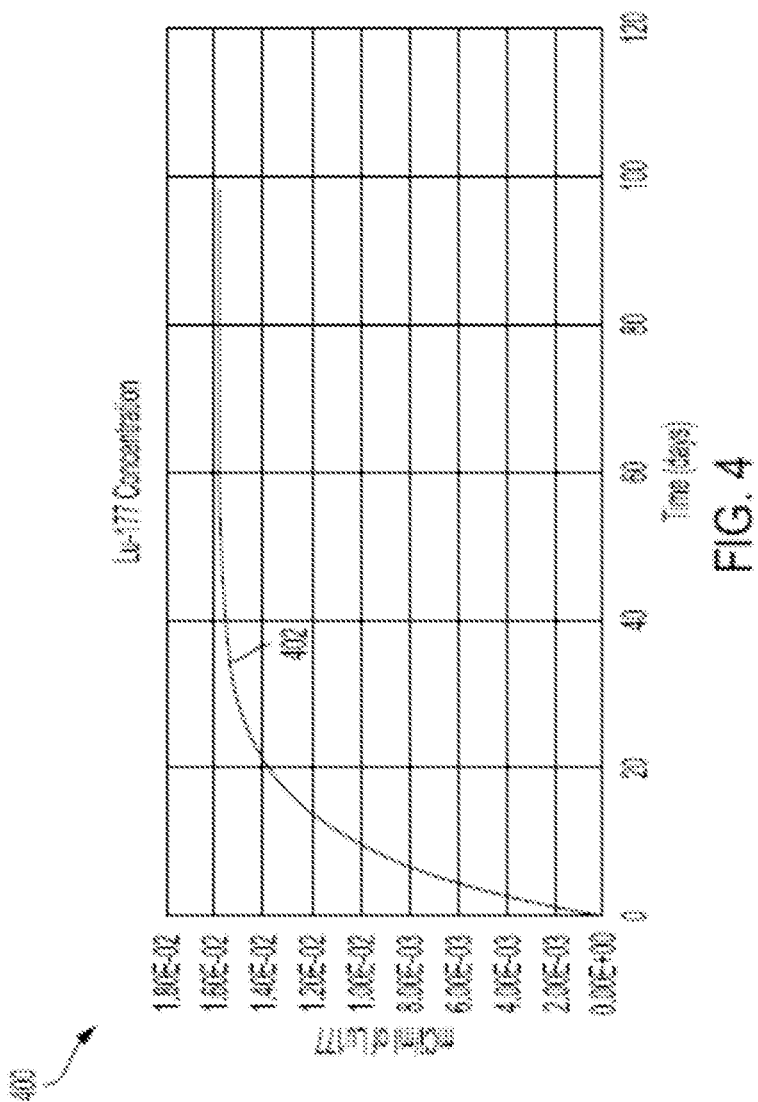
FIG. 4 illustrates a calculation of the activity of the Lu-177 in the Lu-177 dotatate drug as a function of irradiation time in the system shown on FIGS. 2A-2D.

FIG. 4 illustrates a calculation of the activity of the Lu-177 in the Lu-177 dotatate drug as a function of irradiation time in the system shown in FIGS. 2A-2D. The activity quoted by the Lu-177 dotatate drug supplier is 10 mCi/ml of injectable liquid. The Lu-177 activity corresponding to the results provided on FIGS. 2A-2D is approximately 0.015 mCi per ml in equilibrium. This implies that the patient would need to be infused with about 500 ml of solution to receive the same dose of Lu-177 received using 1 ml the currently available drug solution. The application of this method would irradiate a drug molecule precursor in a substantially solid form or alternatively in a liquid or a concentrate form to produce the radioisotope pharmaceutical. In embodiment, the drug molecule precursor is in a substantially solid form, and the irradiated target material (irradiated drug molecule precursor) is reconstituted with a solution (such as an aqueous solution) in the proper proportions to form the final radioisotope pharmaceutical. In embodiments, the irradiation target material includes the drug molecule precursor in liquid form with an aqueous solution in the proper proportions and is then irradiated by neutrons to produce the radioisotope pharmaceutical in the ready-to-use aqueous solution. In embodiments, the drug molecule precursor is in a concentrate form, and the irradiated target material (the irradiated drug molecule precursor) is adjusted with an aqueous solution in the proper proportions to form the ready-to-use radioisotope pharmaceutical.

In embodiments, the application of this method would irradiate an essentially solid version of the desired material composition, such as the solid Lu-176 dotatate precursor molecules, and then create the desired form of the irradiation target from the irradiated solid. For example, the elimination of the inert liquids in the Lu-177 drug injection solution prior to irradiation could increase the Lu-177 in the irradiated material by orders of magnitude. A ready-to-use pharmaceutical aqueous solution with the desired activity per ml could be created by incorporating the irradiated material into a solution in the proper proportions.

Alternatively, the application of this method would irradiate a desired material composition (a drug molecule precursor) in a liquid or concentrate form to produce the radioisotope pharmaceutical which can be a ready-to-use radioisotope pharmaceutical composition or can be further combined with other ingredients such as an aqueous solution to produce the ready-to-use radioisotope pharmaceutical composition.

A ready to use pharmaceutical aqueous solution of the Lu-177 dotatate is discloses in U.S. Pat. Nos. 10,596,276 and 10,596,278, the entire contents of which are incorporated herein by references for all purposes.

The devices shown in FIGS. 2A-2D and 3A-3D also have applications in producing other radioisotopes used in medical and other commercially valuable activities, such as radioactive tracers like Na-24 used for moisture carry-over measurements for Steam Generators, and direct irradiation of an Iodide-salt for thyroid cancer treatments. Other medical treatment radioisotopes, such as Cu-64, Ho-166, P-32, and K-42 could also be produced using the devices shown in FIGS. 2A-2D and 3A-3D.

The method and device shown in the present disclosure provides a novel approach for producing a very promising cancer cure that doesn't require a nuclear reactor to produce the radioisotope or radionuclide needed to combine with relevant peptides, proteins or antibodies to form the final radioisotope drug molecules that are injected into the patients. This approach allows the non-radioactive drug molecule precursors to be constructed in advance of use and subsequently irradiated using electronic neutron generators that minimize the gamma radiation and heat experienced by the drug molecules. This approach will allow the final drug to be produced at a much lower cost and directly in a clinical environment that allows a much more timely patient treatment regimen and more efficient use of the radioisotope.

The method of the present disclosure has another advantages that the non-radioactive drug molecule precursors do not decay and thus have much longer shelf life than their corresponding radioisotope drug molecules in their final forms. The non-radioactive drug molecule precursors can be manufactured in a large scale in advance and stored in hospitals and clinics for multiple applications of PRRT for multiple patients without the need of protective radiation shielding containers or devices. The non-radioactive drug molecule precursors can subsequently be converted to its corresponding radioisotope drug molecules in its final forms immediately before the PRRT proceedings.

The Lu-177 radioisotope pharmaceuticals (final drug products) may further comprise one or more stabilizers against radiolytic degradation such as gentisic or ascorbic acids or their salts during or after the complex formation, preferably after the complex formation.

The method of the present disclosure has further advantages that the Lu-177 radioisotope pharmaceuticals may not need to add any stabilizers against radiolytic degradation such as gentisic or ascorbic acids or their salts, or ethanol that are required in the currently existing Lu-177 radioisotope pharmaceuticals.

As discussed above, currently existing methods for producing the Lu-177 radioisotope pharmaceuticals involves first preparing, purifying, storing and handling before and during the production of the final drug products. One technical problem with these currently existing methods is that the decay of the radionuclide in the intermediate compounds and the final products occurs constantly, e.g. before, during the manufacturing and storage of the drug product, and the released high energy emissions induce the cleavage of the chemical bonds of the molecules which form part of the drug product. This is often referred to as radiolysis or radiolytic degradation. The radiolytic degradation of the receptor binding moiety of the drug may lead to a decrease in its efficacy to act as a diagnostic and/or therapeutic. Stabilizers against radiolytic degradation are typically added in the currently existing Lu-177 radioisotope pharmaceuticals to address this technical problem. However, adding stabilizers may be problematic as those chemicals may have a negative impact on the complexation of the radionuclide into the chelating agent or may have a limited solubility and precipitate from the solution. Ethanol has been reported as stabilizer against radiolysis (WO 2008/009444). While ethanol might not have a negative impact on the complexation or a solubility issue, higher amounts of ethanol in an infusion solution may be physiologically problematic and may have a negative impact on the tolerability of the drug product. In addition, gentisic or ascorbic acids or their salts are reported as stabilizers against radiolytic degradation.

The methods of the present disclosure produce the Lu-177 based radioisotope pharmaceutical (final drug product) directly from a non-radioactive Lu-176 drug molecule precursor without any radioactive intermediate compounds and thus eliminating the need to prepare, purify, storing and handling any radioactive intermediate compounds before or during the production of the final drug products. Therefore, the Lu-177 based radioisotope pharmaceutical (final drug product) of the present disclosure does not require a stabilizer against radiolytic degradation.

The methods, devices and systems of the present disclosure can also be applied to produce Y-90 radioisotope pharmaceuticals to treat cancers such as liver cancer. Current methods for producing Y-90 radioisotope pharmaceuticals are to prepare radioisotope Y-90 compounds first; and then coating micro-spheres the radioactive Y-90 compounds. In contrast, the methods according to the present disclosure are to produce micro-spheres coated with non-radioactive isotope Y-89. The Y-89 coated spheres are then irradiated in the devices shown on FIGS. 2A-2D and 3A-3D until the maximum activity of Y-90 is achieved for use in the treatment of the patient.

The method and device described in this disclosure will allow Applicant to provide the current suppliers of drugs like Lu-177 dotatate with the means to greatly reduce the cost associated with drug production and greatly increase the available supply of highly needed cancer cures. It is estimated that the Lu-177 production market will be $4.25B by 2025. Implementation of the manufacture approach of the present disclosure, could allow Applicant to capture a significant fraction of the supply market.

In various aspects, the present disclosure provides a method for producing a radioisotope pharmaceutical, the method comprising: providing a non-radioactive drug molecule precursor; and irradiating the non-radioactive isotope drug molecule precursor by a neutron flux to convert at least part of the non-radioactive drug molecule precursor to the radioisotope pharmaceutical.

In various aspects, the neutron flux is generated by an electronic neutron generator array having at least one electronic neutron generator.

In various aspects, the method further comprises preparing the non-radioactive isotope drug molecule precursor.

In various aspects, the radioisotope pharmaceutical comprises or is a first complex of a radionuclide and a target cell receptor binding moiety linked to a chelating agent.

In various aspects, the non-radioactive isotope drug molecule precursor comprises or is a second complex of a non-radioactive isotope and the target cell receptor binding moiety linked to the chelating agent, and the non-radioactive isotope is a non-radioactive isotope of the radionuclide or a different metal or metal ion that can be converted to the radionuclide by irradiating non-radioactive isotope using the neutron flux.

In various aspects, the method further comprises preparing the non-radioactive isotope drug molecule precursor by a process, the process comprising: 1) providing a first aqueous solution comprising the non-radioactive isotope; 2) providing a second aqueous solution comprising the target cell receptor binding moiety linked to the chelating agent; 3) mixing the first and second solutions provided in steps 1) and 2) to form a mixture; and 4) heating the mixture to form a reacted solution comprising the second complex, wherein the method comprises irradiating the reacted solution comprising the second complex to convert at least part of the non-radioactive isotope in the second complex to the radionuclide to form the radioisotope pharmaceutical comprising the first complex.

In various aspects, the process further comprises drying and purifying the reacted solution comprising the second complex to form the non-radioactive isotope drug molecule precursor in a solid form.

In various aspects, the target cell receptor binding moiety comprises or is a somatostatin receptor binding peptide selected from the group consisting of octreotide, octreotate, lanreotide, vapreotide and pasireotide, preferably selected from octreotide and octreotate.

In various aspects, the chelating agent is selected from the group consisting of DOTA, DTPA, NT, EDTA, DO3A, NOC and NOTA.

In various aspects, the radioisotope pharmaceutical is selected from the group consisting of a Lu-177 based radioisotope pharmaceutical, an I-131 based radioisotope and a Y-90 based radioisotope pharmaceutical.

In various aspects, the radioisotope pharmaceutical is selected from the group consisting of Lu-177 dotatate, I-131 tositumomab, and Y-90 ibritumomab-tiuxetan.

In various aspects, the non-radioactive drug molecule precursor is selected from the group consisting of a Lu-176 drug molecule precursor, a tellurium drug molecule precursor, and a Y-89 drug molecule precursor.

In various aspects, the non-radioactive drug molecule precursor is selected from the group consisting of Lu-176 dotatate, tellurium tositumomab, and Y-89 ibritumomab-tiuxetan.

In various aspects, the radioisotope pharmaceutical is Lu-177 dotatate, the non-radioactive drug molecule precursor is Lu-176 dotatate. And the Lu-177 dotatate is produced by directly irradiating Lu-176 dotatate by the neutron flux generated by an electronic neutron generator array.

In various aspects, the present disclosure provides a method for producing a Lu-177 based radioisotope pharmaceutical, the method comprising: 1) providing a first aqueous solution comprising non-radioactive Lu-176 isotope; 2) providing a second aqueous solution comprising a target cell receptor binding peptide linked to a chelating agent; 3) mixing the first and second solutions provided in steps 1) and 2) to form a mixture; 4) heating the mixture to form a reacted solution comprising a Lu-176 complex of Lu-176 and the target cell receptor binding peptide linked to the chelating agent; and 5) irradiating the reacted solution comprising the Lu-176 complex to convert at least part of the Lu-176 isotope in the Lu-176 complex to Lu-177 radioisotope to form the Lu-177 based radioisotope pharmaceutical.

In various aspects, the method further comprises drying and/or purifying the reacted solution comprising the Lu-176 complex to form a solid comprising the Lu-176 complex.

In various aspects, the method further comprises drying and/or purifying the reacted solution comprising the Lu-176 complex to form a concentrate comprising the Lu-176 complex.

In various aspects, the target cell receptor binding peptide comprises or is a somatostatin receptor binding peptide.

In various aspects, the somatostatin receptor binding peptide is selected from the group consisting of octreotide, octreotate, lanreotide, vapreotide and pasireotide, preferably selected from octreotide and octreotate.

In various aspects, the somatostatin receptor binding peptide is oxodotreotide.

In various aspects, the chelating agent is selected from the group consisting of DOTA, DTPA, NT, EDTA, DO3A, NOC and NOTA.

In various aspects, the chelating agent is DOTA.

In various aspects, the target cell receptor binding peptide linked to the chelating agent comprises or is dotatate or dotatoc.

In various aspects, the target cell receptor binding peptide linked to the chelating agent comprises or is dotatate.

In various aspects, the Lu-176 complex comprises or is Lu-176 dotatoc or Lu-176 dotatate.

In various aspects, the Lu-176 complex comprises or is Lu-176 dotatate.

In various aspects, the Lu-177 based radioisotope pharmaceutical comprises or is Lu-177 dotatoc or Lu-177 dotatate.

In various aspects, the Lu-177 based radioisotope pharmaceutical comprises or is Lu-177 dotatate.

In various aspects, the present disclosure provides a device for direct production of a radioisotope pharmaceutical from a non-radioactive drug molecule precursor by irradiating the non-radioactive drug molecule precursor using a neutron flux generated by an electronic neutron generator array. The device comprises: the electronic neutron generator array having at least one electronic neutron generator configured to generate the neutron flux; an irradiation module comprising: an irradiation module insertion tube (Rabbit Hole) having an insertion port, a $D_2O$ moderator module surrounding and attached to an outer side surface of the Irradiation module insertion tube, the $D_2O$ moderator module housing $D_2O$ and having an adjustable thickness, a borated water module surrounding and attached to an outer side surface of the $D_2O$ moderator module, and a metallic shielding module surrounding and attached to an outer surface of the borated water module; and an irradiation module insert to be placed in the Irradiation module insertion tube through the insertion port, the irradiation module insert is configured to house an irradiation target material comprising the non-radioactive drug molecule precursor.

In various aspects, irradiation module insert comprises: an insertion rode; a removable nose configured to detachably connect to the insertion rod; an irradiation chamber housed in the removable nose; and an insertion position lock ring configured to be placed on the insertion rod for locking irradiation module insert with the insertion port to adjust a position of the irradiation chamber in the Irradiation module insertion tube, wherein the irradiation target material is housed in the irradiation chamber.

In various aspects, the device further comprises: a radiation detector surrounding and attached to the irradiation chamber for detecting an irradiation level from the irradiation chamber; and a temperature sensor coupled to the irradiation chamber for sensing a temperature of the irradiation chamber.

In various aspects, the device further comprises a control unit configured to connect to the irradiation module and the irradiation module insert.

In various aspects, the irradiation module insert further comprises: an irradiation detector signal output configured to deliver a first signal of the detected irradiation level from the radiation detector to the control unit; and a temperature sensor signal output configured to deliver a second signal of the sensed temperature from the temperature sensor to the control unit.

In various aspects, the at least one electronic neutron generator are configured to direct its neutrons or neutron flux to a center of the Irradiation module insertion tube of the irradiation module.

In various aspects, the irradiation module insert is configured to be placed into the Irradiation module insertion tube and keep the irradiation chamber at the center of the Irradiation module insertion tube and also at the center of the at least one electronic neutron generator so that the neutron flux from the at least one electronic neutron generator are all directed to the irradiation chamber.

In various aspects, the device further comprises a target cooling unit including a liquid coolant, wherein the target cooling unit is configured to attach to the irradiation module to circulate the coolant through the Irradiation module insertion tube for cooling the Irradiation module insertion tube and the irradiation module insert inserted into the Irradiation module insertion tube so to control temperatures inside the Irradiation module insertion tube and thus the irradiation chamber of the irradiation module insert.

In various aspects, the irradiation chamber is a hollow cylinder for housing an irradiation target material and comprises an outer side surface and top and bottom round surfaces, and the irradiation detector is a hollow cylinder concentric with the irradiation chamber and configured to surround the entire outer side surface of the irradiation chamber without covering the top and bottom round surfaces of the irradiation chamber.

In various aspects, the control unit is configured to: 1) receive the second signal; 2) adjust parameters of the target cooling unit to control the temperature inside the Irradiation module insertion tube and the irradiation chamber to maintain within a predetermined temperature range; 3) receive the first signal; 4) determine whether the detected irradiation level reaches a predetermined level; and 5) turn off the at least one electronic neutron generator when the detected irradiation level reaches the predetermined level.

In various aspects, the radioisotope pharmaceutical is selected from the group consisting of a Lu-177 based radioisotope pharmaceutical, an I-131 based radioisotope and a Y-90 based radioisotope pharmaceutical.

In various aspects, the radioisotope pharmaceutical is selected from the group consisting of Lu-177 dotatate, I-131 tositumomab, and Y-90 ibritumomab-tiuxetan.

In various aspects, the non-radioactive drug molecule precursor is selected from the group consisting of a Lu-176 drug molecule precursor, a tellurium drug molecule precursor, and a Y-89 drug molecule precursor.

In various aspects, the non-radioactive drug molecule precursor is selected from the group consisting of Lu-176 dotatate, tellurium tositumomab, and Y-89 ibritumomab-tiuxetan.

In various aspects, the non-radioactive drug molecule precursor comprises or is a Lu-176 complex of Lu-176 and a target cell receptor binding moiety linked to a chelating agent.

In various aspects, the non-radioactive drug molecule precursor comprises or is Lu-176 dotatate.

In various aspects, the radioisotope pharmaceutical comprises or is Lu-177 dotatate.

In various aspects, the irradiation target material is the non-radioactive drug molecule precursor.

All patents, patent applications, publications, or other disclosure material mentioned herein and/or listed in any Application Data Sheet, are hereby incorporated by reference in their entirety as if each individual reference was expressly incorporated by reference respectively. All references, and any material, or portion thereof, that are said to be incorporated by reference herein are incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference and the disclosure expressly set forth in the present application controls.

The present disclosure has been described with reference to various exemplary and illustrative aspects. The aspects described herein are understood as providing illustrative features of varying detail of various aspects of the disclosed disclosure; and therefore, unless otherwise specified, it is to be understood that, to the extent possible, one or more features, elements, components, constituents, ingredients, structures, modules, and/or aspects of the disclosed aspects may be combined, separated, interchanged, and/or rearranged with or relative to one or more other features, elements, components, constituents, ingredients, structures, modules, and/or aspects of the disclosed aspects without departing from the scope of the disclosed disclosure. Accordingly, it will be recognized by persons having ordinary skill in the art that various substitutions, modifications or combinations of any of the exemplary aspects may be made without departing from the scope of the disclosure. In addition, persons skilled in the art will recognize, or be able to ascertain using no more than routine experimentation, many equivalents to the various aspects of the disclosure described herein upon review of this specification. Thus, the disclosure is not limited by the description of the various aspects, but rather by the claims.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although claim recitations are presented in a sequence(s), it should be understood that the various operations may be performed in other orders than those which are described, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "various aspects," "an exemplification," "one exemplification," and the like means that a particular feature, structure, or characteristic described in connection with the aspect is included in at least one aspect. Thus, appearances of the phrases "in one aspect," "in an aspect," "in various aspects," "in an exemplification," and "in one exemplification" in various places throughout the specification are not necessarily all referring to the same aspect. Furthermore, the particular features, structures or characteristics may be combined in any suitable manner in one or more aspects.

As used herein, the singular form of "a", "an", and "the" include the plural references unless the context clearly dictates otherwise.

Directional phrases used herein, such as, for example and without limitation, top, bottom, left, right, lower, upper, front, back, and variations thereof, shall relate to the orientation of the elements shown in the accompanying drawing and are not limiting upon the claims unless otherwise expressly stated.

The terms "about" or "approximately" as used in the present disclosure, unless otherwise specified, means an acceptable error for a particular value as determined by one of ordinary skill in the art, which depends in part on how the value is measured or determined. In certain aspects, the term "about" or "approximately" means within 1, 2, 3, or 4 standard deviations. In certain aspects, the term "about" or "approximately" means within 50%, 200%, 105%, 100%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 100" includes all sub-ranges between (and including) the recited minimum value of 1 and the recited maximum value of 100, that is, having a minimum value equal to or greater than 1 and a maximum value equal to or less than 100. Also, all ranges recited herein are inclusive of the end points of the recited ranges. For example, a range of "1 to 100" includes the end points 1 and 100. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

In describing aspects and embodiments of the present application, specific terminology is employed for the sake of clarity. However, the disclosure is not intended to be limited to the specific terminology so selected. Nothing in this specification should be considered as limiting the scope of the present disclosure.

All examples presented are representative and non-limiting. The above-described aspects and embodiments may be modified or varied, without departing from the disclosure, as appreciated by those skilled in the art in light of the above teachings. It is therefore to be understood that, within the scope of the claims and their equivalents, the disclosure may be practiced otherwise than as specifically described.

Without further elaboration, it is believed that one skilled in the art can use the preceding description to utilize the claimed disclosures to their fullest extent. The examples, aspects and embodiments disclosed herein are to be construed as merely illustrative and not a limitation of the scope of the present disclosure in any way. It will be apparent to those having skill in the art that various changes and modifications may be made to the details of the above-described aspects and embodiments without departing from the underlying principles discussed. In other words, various modifications and improvements of the aspects and embodiments specifically disclosed in the description above are within the scope of the appended claims. For example, any suitable combination of features of the various aspects and embodiments described is contemplated. Note that elements recited in means-plus-function format are intended to be construed in accordance with 35 U.S.C. § 112 ¶6. The scope of the disclosure is therefore defined by the following claims.

What is claimed is:

1. A method for producing a radioisotope pharmaceutical, the method comprising:
   mixing a first aqueous solution comprising a non-radioactive Lu-176 isotope and a second aqueous solution comprising a target cell receptor binding peptide linked to a chelating agent to form a reacted solution comprising a Lu-176 complex of the Lu-176 isotope and the target cell receptor binding peptide linked to the chelating agent; and
   irradiating the Lu-176 complex by a neutron flux generated by an electronic neutron generator and concurrently cooling the Lu-176 complex to convert the Lu-176 isotope in the Lu-176 complex to a Lu-177 radioisotope to form a Lu-177 based radioisotope pharmaceutical.

2. The method of claim 1, wherein the target cell receptor binding peptide comprises or is a somatostatin receptor binding peptide selected from the group consisting of octreotide, octreotate, lanreotide, vapreotide and pasireotide, and wherein the chelating agent is selected from the group consisting of DOTA, DTPA, NT, EDTA, DO$_3$A, NOC and NOTA.

3. The method of claim 2, further comprising
   heating the mixture of the first aqueous solution and the second aqueous solution to form the reacted solution comprising the Lu-176 complex.

4. The method of claim 3, further comprising drying and purifying the reacted solution comprising the Lu-176 complex to form a non-radioactive isotope drug molecule precursor in a solid form, wherein irradiating the Lu-176 complex comprises irradiating the non-radioactive isotope drug molecule precursor in the solid form.

5. A device for direct production of a radioisotope pharmaceutical from a non-radioactive drug molecule precursor by irradiating the non-radioactive drug molecule precursor using a neutron flux generated by an electronic neutron generator array, the device comprising:
   at least one electronic neutron generator configured to generate the neutron flux;
   an insertion tube extending along an axis of the device, wherein the insertion tube is externally accessible via an insertion port;
   a D$_2$O moderator module surrounding and attached to an outer side surface of the insertion tube, the D$_2$O moderator module housing D$_2$O;
   a borated water module surrounding and attached to an outer side surface of the D$_2$O moderator module;
   a metallic shielding module surrounding and attached to an outer surface of the borated water module; and
   an irradiation module insert insertable in the insertion tube via the insertion port, wherein the irradiation module insert comprises:
      an insertion rod for inserting the irradiation module insert in the insertion tube;
      an irradiation chamber for housing an irradiation target material comprising the non-radioactive drug molecule precursor;
      a removable nose configured to detachably connect to the insertion rod, wherein the irradiation chamber is housed in the removable nose; and
      an insertion position lock ring configured to be placed on the insertion rod for locking the irradiation module insert with the insertion port to adjust a position of the irradiation chamber in the irradiation insertion tube.

6. The device of claim 5, further comprising:
   a radiation detector surrounding and attached to the irradiation chamber for detecting an irradiation level from the irradiation chamber; and
   a temperature sensor coupled to the irradiation chamber for sensing a temperature of the irradiation chamber.

7. The device of claim 6, further comprising a control unit configured to connect to the radiation detector and the temperature sensor.

8. The device of claim 7, wherein the irradiation module insert further comprises:
   an irradiation detector signal output configured to deliver a first signal of the detected irradiation level from the radiation detector to the control unit; and
   a temperature sensor signal output configured to deliver a second signal of the sensed temperature from the temperature sensor to the control unit.

9. The device of claim 8, wherein the at least one electronic neutron generator is configured to direct the neutron flux to a center of the insertion tube.

10. The device of claim 9, wherein the irradiation module insert is configured to be placed into the insertion tube such that the irradiation chamber is exposed to the neutron flux from the at least one electronic neutron generator.

11. The device of claim 10, further comprising a target cooling unit including a liquid coolant, wherein the target cooling unit is configured to circulate the coolant through the insertion tube for cooling the irradiation module insert inserted into the insertion tube to control temperatures inside the irradiation chamber.

12. The device of claim 11, wherein the irradiation chamber is a hollow cylinder for housing the irradiation target material and comprises an outer side surface and top and bottom round surfaces, and wherein the irradiation detector is a hollow cylinder concentric with the irradiation chamber and configured to surround the entire outer side surface of the irradiation chamber without covering the top and bottom round surfaces of the irradiation chamber.

13. The device of claim 12, wherein the control unit is configured to:
   1) Receive the second signal; 2) adjust parameters of the target cooling unit to control the temperature inside the insertion tube and the irradiation chamber to maintain the temperature within a predetermined temperature range; 3) receive the first signal; 4) determine whether the detected irradiation level reaches a predetermined level; and 5) turn off the at least one electronic neutron generator when the detected irradiation level reaches the predetermined level.

14. The device of claim 5, wherein the radioisotope pharmaceutical is selected from the group consisting of a Lu-177 based radioisotope pharmaceutical, an I-131 based radioisotope pharmaceutical and a Y-90 based radioisotope pharmaceutical.

15. The device of claim 14, wherein the non-radioactive drug molecule precursor is selected from the group consisting of a Lu-176 drug molecule precursor, a tellurium drug molecule precursor, and a Y-89 drug molecule precursor.

16. The device of claim 5, wherein the radioisotope pharmaceutical is selected from the group consisting of Lu-177 dotatate, I-131 tositumomab, and Y-90 ibritumomab-tiuxetan, and wherein the non-radioactive drug molecule precursor is selected from the group consisting of Lu-176 dotatate, tellurium tositumomab, and Y-89 ibritumomab-tiuxetan.

17. The method of claim 2, wherein irradiating the Lu-176 complex by the neutron flux generated by the electronic neutron generator and concurrently cooling the Lu-176 complex comprises irradiating and cooling the Lu-176 complex using a device, wherein the device comprises:
the electronic neutron generator;
an insertion tube extending along an axis of the device, wherein the insertion tube is externally accessible via an insertion port;
a $D_2O$ moderator module surrounding the insertion tube;
a borated water module surrounding the $D_2O$ moderator module;
a metallic shielding module surrounding the borated water module; and
an irradiation module insert insertable in the insertion tube via the insertion port, wherein the irradiation module insert comprises:
an insertion rod for inserting the irradiation module insert in the insertion tube; and
an irradiation chamber for housing the non-radioactive isotope drug molecule precursor; and
a cooling unit including a coolant, wherein the cooling unit is to circulate the coolant through the insertion tube for cooling the irradiation module insert inserted into the insertion tube.

18. A device comprising:
an insertion tube extending along a central axis of the device, wherein the insertion tube is externally accessible via an insertion port;
a neutron moderator circumferentially surrounding the insertion tube;
borated water circumferentially surrounding the moderator module;
shielding circumferentially surrounding the borated water;
an electronic neutron generator to generate neutron flux, wherein the electronic neutron generator extends radially through the shielding and the borated water such that an active end of the electronic neutron generator is positioned proximate to the neutron moderator;
an irradiation module insert insertable in the insertion tube via the insertion port, wherein the irradiation module insert comprises:
an insertion rod for inserting the irradiation module insert in the insertion tube; and
an irradiation chamber coupled to the insertion rod for housing a non-radioactive drug molecule precursor, wherein the irradiation chamber is positionable to be exposed to the neutron flux generated by the electronic neutron generator when the irradiation module insert is inserted in the insertion tube; and
a cooling unit including a coolant, wherein the cooling unit is to circulate the coolant through the insertion tube for cooling the irradiation module insert inserted into the insertion tube.

19. The device of claim 18, wherein the electronic neutron generator comprises a plurality of electronic neutron generators, wherein each of the plurality of electronic neutron generators extends radially through the shielding and the borated water such that the active ends of the plurality of electronic neutron generators are positioned proximate to the neutron moderator.

20. The method of claim 1, wherein the Lu-176 complex comprises Lu-176 dotatate, and wherein the Lu-177 based radioisotope pharmaceutical comprises Lu-177 dotatate.

* * * * *